US006899728B1

(12) United States Patent  (10) Patent No.: US 6,899,728 B1
Phillips et al.  (45) Date of Patent: May 31, 2005

(54) REINFORCED GRAFT

(75) Inventors: Peter Phillips, Abingdon (GB); Julian Ellis, Nottingham (GB); Alan McLeod, Somerset (GB); Gail Beaton, Oxon (GB); Peter Butcher, Nottingham (GB)

(73) Assignees: Bridport (UK) Limited, Dorset (GB); Anson Medical Limited, Abingdon (GB)

( * ) Notice: Subject to any disclaimer, the term of this patent is extended or adjusted under 35 U.S.C. 154(b) by 0 days.

(21) Appl. No.: 09/601,023

(22) PCT Filed: Jan. 26, 1999

(86) PCT No.: PCT/GB99/00261

§ 371 (c)(1),
(2), (4) Date: Jul. 26, 2000

(87) PCT Pub. No.: WO99/37242

PCT Pub. Date: Jun. 29, 1999

(30) Foreign Application Priority Data

Jan. 26, 1998 (GB) .................................... 9801660
Jan. 31, 1998 (GB) .................................... 9802060

(51) Int. Cl.[7] .............................................. A61F 2/04
(52) U.S. Cl. ...................... 623/1.13; 623/901; 600/36
(58) Field of Search ............................. 623/1.13, 901, 623/1.15, 1.22, 1.32; 139/387 R

(56) References Cited

U.S. PATENT DOCUMENTS

| 4,503,569 A | 3/1985 | Dotter ........................ 623/1.19 |
| 4,512,338 A | 4/1985 | Balko et al. ................. 606/108 |
| 4,800,882 A | 1/1989 | Gianturco |
| 4,907,336 A | 3/1990 | Gianturco |
| 5,015,253 A | 5/1991 | MacGregor ................ 623/1.15 |
| 5,041,126 A | 8/1991 | Gianturco |
| 5,161,547 A | 11/1992 | Tower ........................ 606/198 |
| 5,226,913 A | 7/1993 | Pinchuk ..................... 623/1.15 |
| 5,282,824 A | 2/1994 | Gianturco .................. 623/1.13 |
| 5,314,444 A | 5/1994 | Gianturco |
| 5,389,106 A | 2/1995 | Tower ........................ 623/1.15 |
| 5,403,341 A | 4/1995 | Solar ......................... 623/1.11 |
| 5,507,771 A | 4/1996 | Gianturco .................. 606/198 |
| 5,562,697 A | 10/1996 | Christiansen .............. 623/1.16 |
| 5,575,816 A | 11/1996 | Rudnick et al. ........... 623/1.15 |
| 5,591,230 A | 1/1997 | Horn et al. ................ 623/1.17 |
| 5,601,593 A | 2/1997 | Freitag ...................... 623/1.19 |
| 5,718,724 A | 2/1998 | Goicoechea et al. ....... 606/194 |
| 5,733,325 A | 3/1998 | Robinson et al. .......... 623/1.11 |
| 5,746,766 A | 5/1998 | Edoga ....................... 623/1.2 |
| 5,782,904 A | 7/1998 | White et al. |
| 5,843,117 A * | 12/1998 | Alt et al. ................... 623/1.15 |
| 5,891,193 A | 4/1999 | Robinson et al. .......... 128/898 |
| 5,935,161 A | 8/1999 | Robinson et al. .......... 623/921 |

(Continued)

FOREIGN PATENT DOCUMENTS

DE 4446036 A1 * 7/1996

(Continued)

*Primary Examiner*—Brian E Pellegrino
(74) *Attorney, Agent, or Firm*—Craig A. Fieschko, Esq.; DeWitt Ross & Stevens S.C.

(57) ABSTRACT

A graft is provided with a flexible sheet of graft material to which is sewn a reinforcing wire, preferably of shape-memory alloy. Sewing of the wire is carried out while the sheet is substantially planar, thus by conventional embroidery machines. The sheet is subsequently rolled into a tubular shape.

23 Claims, 28 Drawing Sheets

U.S. PATENT DOCUMENTS

| | | | |
|---|---|---|---|
| 5,980,565 A | 11/1999 | Jayaraman | 623/1.12 |
| 6,024,763 A | 2/2000 | Lenker et al. | 606/191 |
| 6,042,605 A * | 3/2000 | Martin et al. | 623/1.13 |
| 6,475,232 B1 * | 11/2002 | Babbs et al. | 623/1.13 |

FOREIGN PATENT DOCUMENTS

| | | | |
|---|---|---|---|
| WO | WO 95/08966 A1 | | 4/1995 |
| WO | WO 95/26695 | | 10/1995 |
| WO | WO 97/09007 A1 | * | 3/1997 |
| WO | WO 97/25002 | | 7/1997 |
| WO | WO 97/33532 A2 | * | 9/1997 |
| WO | WO 98/07385 | | 2/1998 |
| WO | WO 98/07386 | | 2/1998 |
| WO | WO 98/20810 | | 6/1998 |
| WO | 98/25544 | * | 9/1998 |
| WO | WO 99/62431 | | 9/1999 |

* cited by examiner

REINFORCED GRAFT

FIELD OF THE INVENTION

This invention relates to a reinforced graft and to a method of producing such a graft which may be used for the treatment of aneurysms, eg in the aorta, by an endoluminal technique, which is minimally invasive and which can therefore be used on many patients who are too old or frail to be able to withstand conventional surgery.

BACKGROUND OF THE INVENTION

Conventional vascular grafts commonly consist of a textile or polymer tube which is implanted into a patient in a major open surgical procedure, grafts which have been implanted endoluminally, that is from within the vessel, consist of grafts which are combined with stents. Such grafts are very time-consuming to produce and this causes particular problems when a bespoke graft is required to be produced at short notice.

Additionally, one of the major problems of existing vascular grafts for endoluminal surgery is that, because of the tortuous bends commonly encountered between the aorta and iliac arteries of patients with aneurysms, there is a tendency for existing tubular grafts to collapse at least partially. This is because, when the tube is curved for any reason, the external diameter of the curve is necessarily longer than the internal, and the excess graft material on the internal diameter of the curve kinks into the lumen, thereby narrowing or even closing it completely. This problem also arises in vascular grafts for repair of, for example, the popliteal artery because of the extreme bending movements which are imparted to this artery during knee flexion.

Furthermore once a graft has been introduced into an artery by the surgeon and located at the correct position, it is necessary to ensure that it is reliably held at such position.

Some devices in use to date are based upon the combination of a stent with a graft, a stent being a relatively rigid metallic cylinder with highly fenestrated walls. This produces a strong implant but one which is relatively inflexible. A frequent complication of arterial disease is the development of highly tortuous vessels through which it is very difficult to pass substantially rigid graft stents.

Most graft stents require the inflation of a balloon inside them to expand the graft to fit within the blood vessel although self expanding designs have been recently introduced.

Most existing designs involve the use of a preformed stent which usually involves expensive construction techniques such as laser cutting and plasma welding.

In attaching the preformed stent to the graft, current devices usually involve multiple individual stitches around the stent and attached to the graft. These stitches are necessarily attached by hand in a costly and time consuming process.

A further problem with the current designs, arising from the substantial stent components, is the difficulty in designing bifurcated grafts which can be used at, for instance, the aorto-iliac bifurcation.

A further problem associated with long graft stents, particularly in the arteries of the lower limb, is irritation of the arteries arising from trauma of insertion and the longer term presence of the synthetic material.

SUMMARY OF THE INVENTION

The present invention seek to provide an improved reinforced graft and method of making such a graft.

According to an aspect of the present invention, there is provided a graft including a sheet of flexible material, a plurality of reinforcement elements extending transversely relative to a longitudinal direction of the sheet of material, the reinforcement elements being spaced from one another in the longitudinal direction, wherein at least some of the plurality of reinforcement elements are formed from a continuous wire.

Advantageously, the sheet of material is formed as a tube with the reinforcement elements extending annularly around the tube.

The reinforcement elements are preferably compressible radially relative to the tube.

When the graft is formed into its in-use shape, the reinforcing elements are preferably pre-stressed. This enables the use of reinforcement elements which are more deformable than prior art devices.

According to another aspect of the present invention, there is provided a graft including at least one radio-opaque marker embroidered onto the graft. Advantageously, the marker provides an indication of the part of the graft to which the marker is embroidered. For example, the marker could denote an "L", "R", "A" or "P" denoting, respectively, left, right, anterior and posterior. A plurality of opaque markers could be provided on the graft.

It will be apparent that an embroidered marker could also be provided on a stent by providing embroiderable material on the stent.

According to another aspect of the present invention there is provided a graft or stent including at one extremity thereof a plurality of flexible members extending in a longitudinal direction of the graft or stent from an annular perimeter thereof, an annulus being provided at a free extremity of the flexible members, the flexible members being deformable substantially to a point to provide a flexible neck about which the annulus can rotate. This structure can provide a front guide to the graft or stent considerably facilitating insertion of the graft or stent into, for example, an artery, and greatly improving fixation in highly tortuous vessels.

Preferably, the elongate members provide a flow path into the graft or stent.

In the preferred embodiment, the elongate members are provided with barbs at their extremities remote from the graft or stent, for fixing the graft or stent into, for example, an artery. Alternatively, separate barbs may be provided on the annulus.

According to another aspect of the present invention, there is provided a method of forming a reinforced graft, including providing a sheet of material, a plurality of reinforcement elements in substantially flat configuration, sewing the reinforced elements to the fabric, forming the fabric into a substantially tubular shape.

This method enables the graft to be produced by conventional sewing machines.

Preferably, the method includes a step of sewing guides over the reinforcement elements, moving the reinforcement elements into their correct position on the sheet of material, and then sewing the reinforcement elements into substantially fixed positions on the sheet of material.

Advantageously, the reinforcement elements are sewn loosely onto the sheet of material. For example, spaced stitches could be used to enable slight buckling of the material between stitches during compression of the graft.

Alternatively, stitches which have a stitch width of 2 to 9 times the width of the reinforcement elements could be used.

Advantageously, a reduced friction coated yarn is used to enable some movement of the reinforcement elements relative to the sheet of material, particularly on compression of the finished graft.

In the preferred embodiment, the reinforcement elements are provided by a single wire sewn into a ladder of substantially straight portions connected by substantially U-shaped connecting portions. The connecting portions may be round or substantially square in shape.

Advantageously, the graft is formed so that connecting portions overlap. In the preferred embodiment overlapping connection portions are sewn to one another.

According to another aspect of the present invention, there is a provided a method of forming a reinforced graft or stent in which reinforcement elements are connected to a flexible fabric sheet by means of a lock-stitch or chain-link.

According to another aspect of the present invention, there is provided a reinforced graft including a sheet of flexible material and a plurality of reinforcement elements, the reinforcement elements being substantially parallel to the weft or warp of the fabric. Providing reinforcement elements substantially parallel to the weft or warp of the fabric provides a stable and substantially inelastic, non-expandable structure. On the other hand, providing reinforcement elements at substantially 45° to the weft or warp provides a more elastic device.

The preferred embodiment can provide a reinforced graft which is sufficiently flexible to allow it to be drawn through tortuous vessels and which has sufficient radial stiffness to resist kinking and subsequent collapse which would occlude the flow of blood through the graft. It can be used for endovascular implantation in diseased arteries such as the aorta, carotid, iliac, femoral and popliteal arteries. Other applications of the device exist in vessels in the body such as veins, bile ducts, oesophagus, trachea etc.

Preferably, the reinforced graft is self expanding to the extent that it does not require a balloon for inflation.

Advantageously, the reinforced graft does not involve the separate manufacture and attachment of a stent and can be manufactured simply and relatively quickly. The simplicity of the preferred construction is intended to assist in the production of bifurcated, tapered and connecting grafts.

It is preferred that the graft is sufficiently supple that it can be everted so that when initially inserted, the proximal part of the graft can be held and the distant part pulled through the proximal part so that finally, the graft is everted end to end. This possibility reduces the trauma of implanting long lengths of graft.

An example of a method of producing a reinforced graft comprises the steps of attaching filamentary reinforcing material to a sheet of flexible graft material having opposite side edges so that the reinforcing material extends laterally over the sheet with respect to the opposite side edges and is preferably attached along substantially the whole of its length to the sheet; forming the sheet into a tube having a longitudinal seam; and preferably securing together the reinforcing material on opposite sides of the longitudinal seam.

In this example, the reinforcing material can be very accurately and conveniently attached at the required places to the sheet when the latter is laid out flat and before the sheet is formed into a tube, thus avoiding the complication of attaching the reinforcing material to a pre-formed tube of graft material.

Preferably, the filamentary reinforcing material is attached to the sheet of flexible graft material so as to define a sinuous pattern of the reinforcing material in which a multiplicity of substantially linear regions extending laterally with respect to the sheet are joined by bends, and the bends at one side of the sinuous pattern are secured to corresponding regions of the reinforcing material at the other side. In this way, spaced hoops of filamentary reinforcing material are provided which are secured to the tube, the hoops being spaced apart in the longitudinal direction of extent of the tube. It will be understood that these hoops can be appropriately spaced apart so as to permit the required flexibility of the tube to enable it to be bent around tortuous bends commonly encountered in the arteries of patients whilst still supporting the tube in such a way as to prevent kinking thereof exclusively in a localised region. Thus, when the tube is bent, it is constrained to bend in a series of small kinks between the reinforcing hoops, and thereby able to follow curvatures encountered in practice without significant stenosis of the lumen.

In a particularly preferred embodiment, the bends are secured using ties which are not passed through the wall of the tube. This may be effected simply by passing the ties solely around the part of the filamentary material to be joined together and knotting them.

The seam in the tube is preferably formed by securing the sheet along the side edges and then folding the portion of the tube in the region of the seam so that the fold is disposed on the outside of the tube.

Another example of a method of producing a reinforced graft comprises the steps of securing filamentary anchor material to flexible graft material by attaching it to the graft material over a plurality of spaced bends in the filamentary anchor material; and cutting the filamentary material at regions between the bends so as to form a multiplicity of bristles or barbs of the filamentary material which project from the flexible graft material.

The bristles or barbs (hereinafter generally referred to simply as bristles) act as effective anchors which retain the graft in place in use and may even be longer than the thickness of the wall of the artery or other organ into which the graft is to be fitted.

Preferably, the flexible graft material is in the form of a sheet, and this method includes the step of forming the sheet into a tube so that the filamentary anchor material is disposed on the outer surface of the tube. The cutting step may be performed before the tube is formed but is preferably performed after.

Preferably, the bends are formed so that, although they may all face in the same general direction relative to the direction of extent of the tube, some of the bristles extend from the bends at different angles relative to others in the direction of extent of the tube. This may be achieved by making some of the bends tighter than others.

The sheet of flexible graft material may be a woven or non-woven fabric formed e.g. of a suitable bio-compatible polymer such as a bio-compatible polyester. A woven polyester microfibre (typically, 6–7 $\mu$m diameter fibre) fabric is particularly preferred, which may be coated for example with gelatine or other material to enhance tissue in-growth or reduce thrombogenicity or permeability.

The filamentary material may be attached to one surface of the sheet by gluing or welding. However, it is preferred to effect the attachment by stitching, preferably using a computer controlled embroidery machine. Stitching may be effected over substantially the whole of the length of the filamentary reinforcing material which is fully secured to the sheet of flexible graft material and thus incapable of being displaced relative to the sheet.

The filamentary material is preferably a material having super-elastic and/or shape-memory properties, e.g. a super-elastic, shape-memory alloy such as a nickel-titanium alloy (e.g. Nitinol—50Ni/50Ti), and is preferably also in the form of a wire. The wire may have a diameter of about 0.2 mm. However, it is within the scope of the present invention for the reinforcing material to be any suitable bio-compatible material suitable for implantation, for example nylon, polyester, silk, polyglycolic acid, polyactic acid, metal or alloy or any combination thereof.

The preferred embodiment includes a combination of the features and methods described herein. Thus, it is preferred for portions of the filamentary reinforcing material used in the first method described above to define the plurality of bends provided in the second method described above. In such a case, the filamentary reinforcing material is chosen to be sufficiently rigid to impart the required anchor properties of the bristles formed from the bends.

A spring structure may be provided at one or both ends of the tubular graft so as to assist in retention of the tubular graft against the wall of the artery in which the graft is in use located.

An example of reinforced graft comprises a tubular body formed of flexible graft material, and a filamentary reinforcing material secured to the graft material in a pattern such that the filamentary reinforcing material extends around the tube and longitudinally thereof to allow the thus-reinforced tubular body to bend, wherein the pattern is defined whilst the filamentary reinforcing material is being secured to the graft material. This can be achieved before the tubular body is formed from a sheet of the graft material as described above, or it may be achieved by securing the filamentary reinforcing material to the pre-formed tubular body. The pattern may be a helical arrangement of the filamentary reinforcing material around the tubular body, or it may be a sinuous arrangement as described above. A sinuous arrangement where opposed bends are overlapped and interdigitated (see below) can assist in imparting columnar strength to the tubular body.

Typically in the embodiments described herein the reinforcement does not constitute a stand-alone stent.

BRIEF DESCRIPTION OF THE DRAWINGS

Various embodiments of the present invention are described below, by way of example only, with reference to the accompanying drawings, in which.

DETAILED DESCRIPTION OF THE INVENTION

In the preferred embodiments described below, the graft comprises a textile polymer sheet which can be either flat or preformed into a tube. The sheet is subsequently reinforced by attaching one or more lengths of fine wire to the material, either by stitching to the surface, threading through pockets formed in the material, threading the wire through the body of the material by weaving, braiding or knitting the wire into the body of the material at the time of manufacture.

A convenient method of rapidly applying the wire to flat fabric described in detail below, is by the use of a computer controlled embroidery machine which is used to form stitches over the wire and attach it to the fabric. This technique is restricted by available machinery to flat fabric which is subsequently rolled and joined to form a tube.

Alternative methods of construction allow the wire to be attached to tubular devices, obviating the need for a join along the length of the device. Such joins have been implicated in longer term failures of some implants.

The pattern in which the wire is laid on the fabric is important for achieving satisfactory mechanical characteristics. The wire is arranged to run approximately circumferentially around the graft, and approximately perpendicular to the long axis of the device. The wire is placed along the length of the graft and each approximately circumferential section can be connected to other circumferential sections so that, in the limit, the entire graft can be reinforced by a single wire.

The intervals between each successive approximately circumferential turn are significant for it is between these parts that the fabric of the graft can produce small buckles, allowing the overall graft to be bent and folded without collapsing the cross-section.

Figure 1:
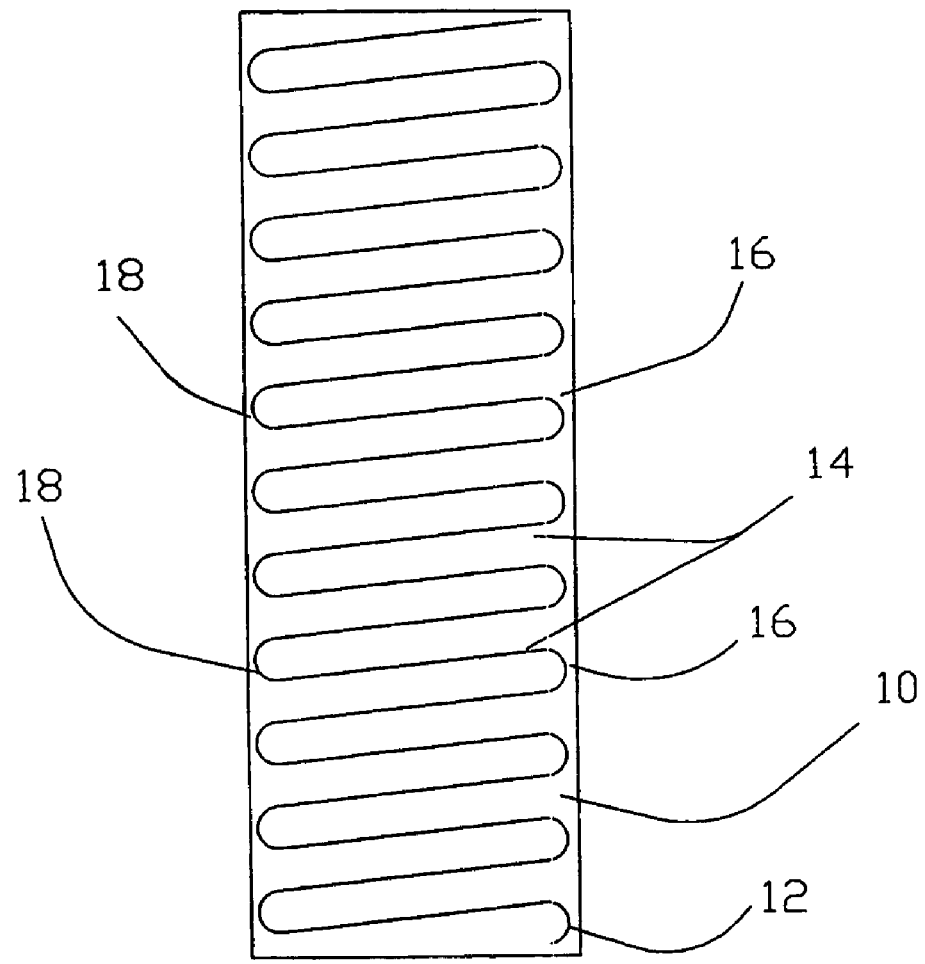
FIG. 1 is a schematic diagram of a first embodiment of reinforced graft prior to rolling into a tubular shape.

Referring to FIG. 1, the embodiment of reinforced graft shown includes a sheet of fabric 10 of the type used for grafts. Onto this sheet 10 is laid a wire 12 which is preferably pre-arranged in a substantially flat ladder pattern in which the straight portions 14 of the wire 12 may lie either perpendicular to the longitudinal axis of the sheet 10 or at a slight angle to the normal to this axis.

Figure 3A:
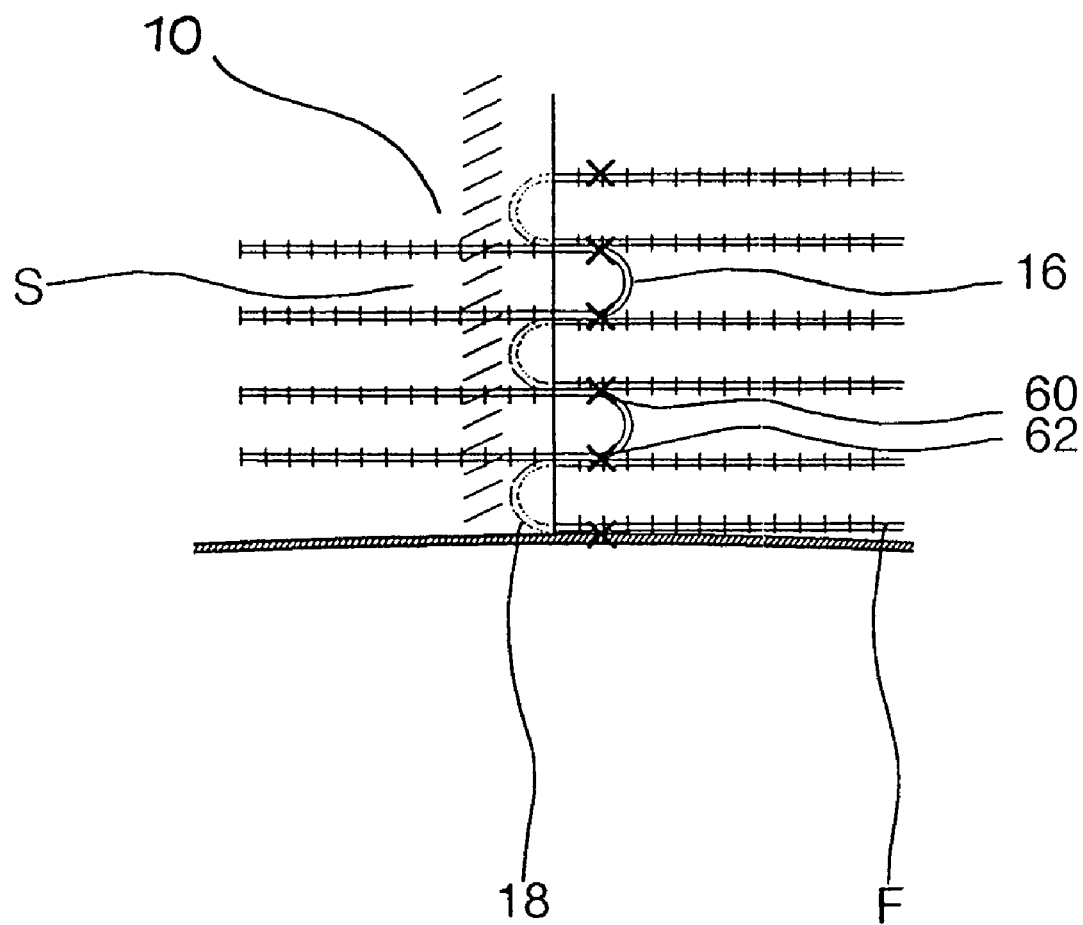
FIG. 3a is a schematic diagram of part of the graft of FIG. 1 or FIG. 2 when rolled into a tubular or frusto-conical shape.
Figure 3B:
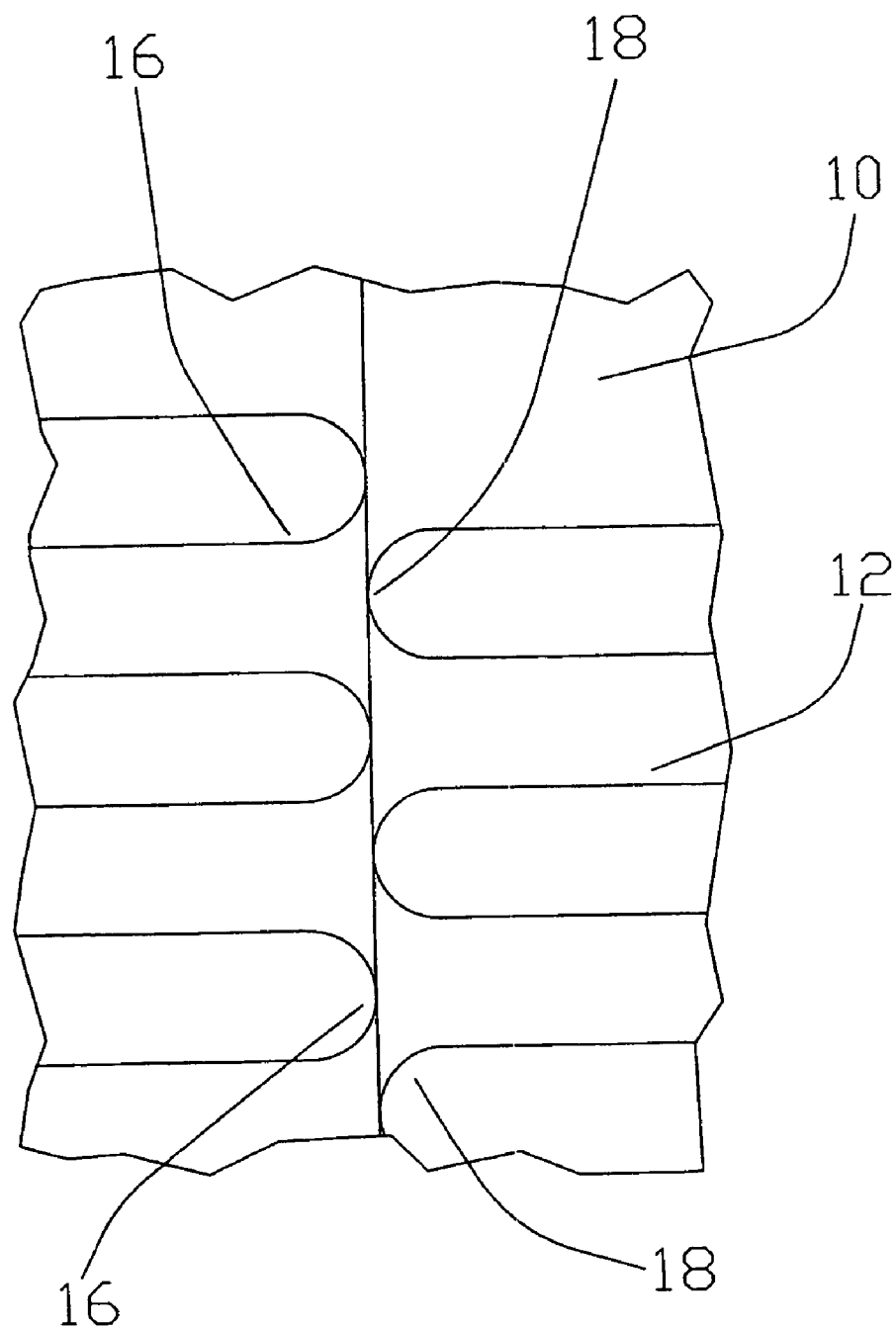
FIG. 3b is a schematic diagram similar to FIG. 3a, showing interdigitation of adjacent rung ends.

The embodiment as shown in FIG. 1 is in use rolled into a tube such that the opposed rounded ends 16, 18 of the wire ladder 12 become located adjacent to one another. When the straight portions 14 of the wire lie perpendicular to the longitudinal axis of the sheet 10, the rounded ends 16, 18 of the wire 12 interdigitate, as can be seen in FIGS. 3a and 3b. This is described in further detail below.

On the other hand, when the straight portions 14 of the wire ladder 12 are disposed at the appropriate angle to the perpendicular, the opposing rounded ends 16, 18 can be made to oppose or overlap one another, in the manner shown in FIGS. 6a and 6b, also described in further detail below.

Figure 2:
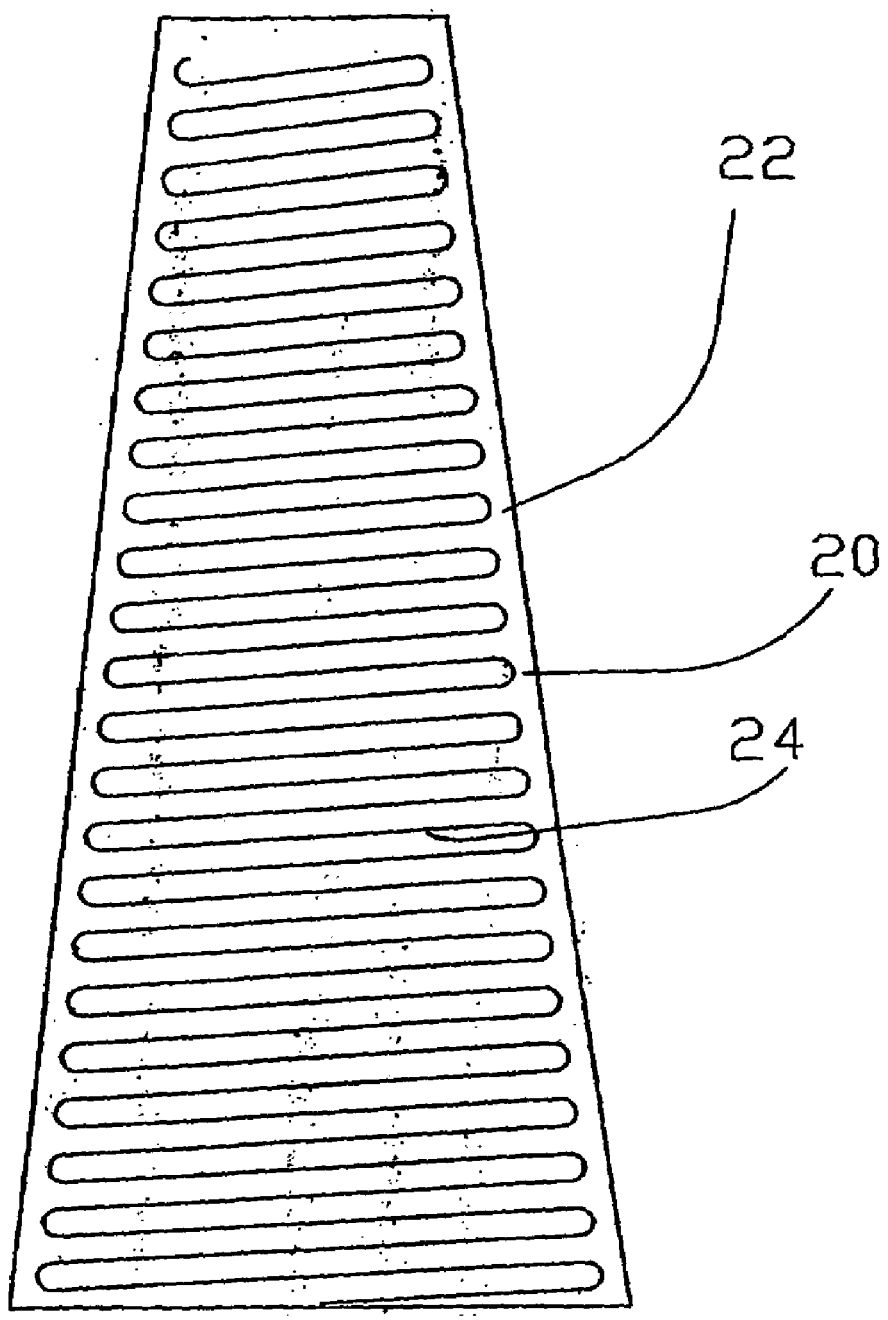
FIG. 2 is a schematic diagram of a second embodiment of reinforced graft prior to rolling into a frusto-conical shape.

FIG. 2 shows another embodiment of reinforced graft which includes a sheet of graft material 20 which tapers from one end to the other in a longitudinal direction of the sheet 20 and a wire 22 of reinforcement material configured in ladder-type fashion and which tapers in a similar manner to the sheet 20.

The straight portions 24 of the reinforcement wire 22 can lie perpendicular to the longitudinal axis of the sheet 20 or at a slight angle thereto, in a similar manner to the embodiment of FIG. 1, so as to produce the effects shown in FIGS. 3a, 3b, 6a and 6b.

Figure 4:
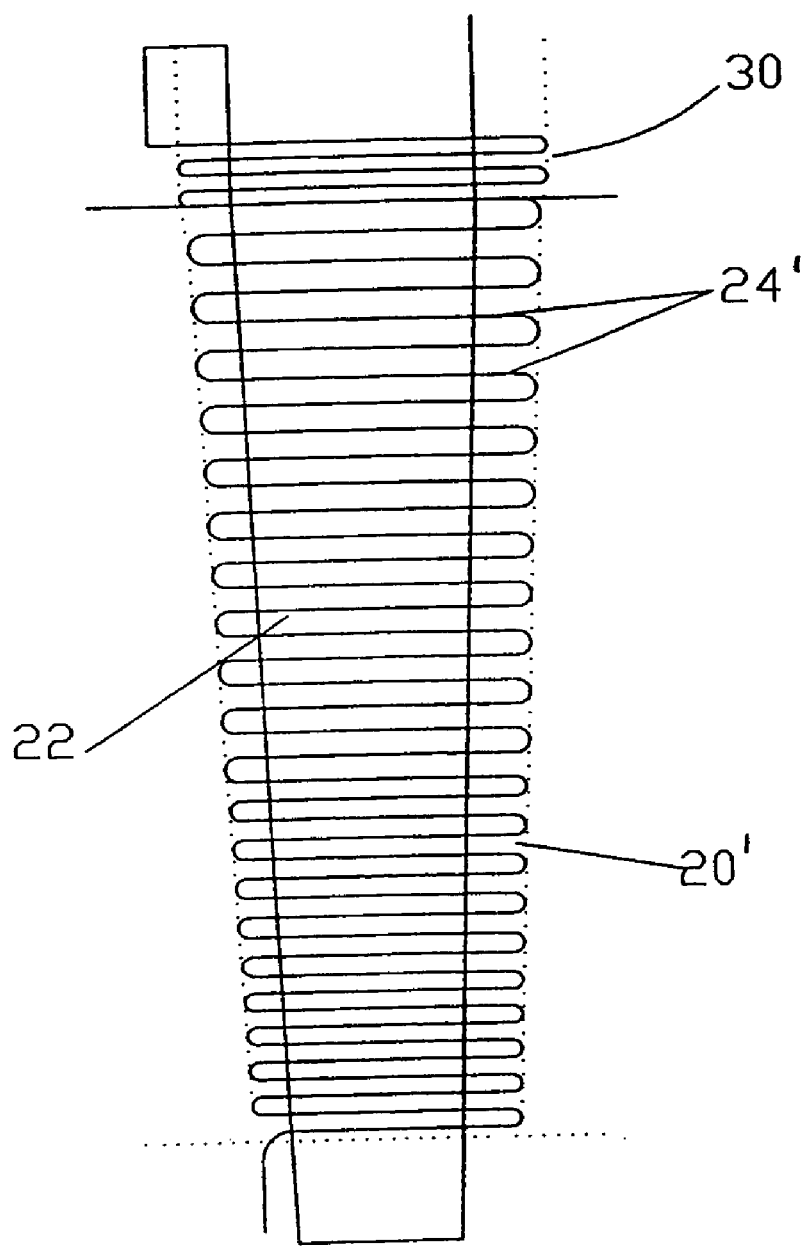
FIG. 4 is a schematic diagram of another embodiment of reinforced graft prior to rolling into a frusto-conical shape.

FIG. 4 shows an embodiment of reinforced graft similar to that of FIG. 2, in which the straight portions 24' lie perpendicular to the longitudinal axis of the sheet 20' and in which at the wide end of the sheet 20' there is provided a portion 30 of wire 20' in which the individual "rungs" have a much tighter pitch. This produces a stiffer opening into the graft.

Figure 5:
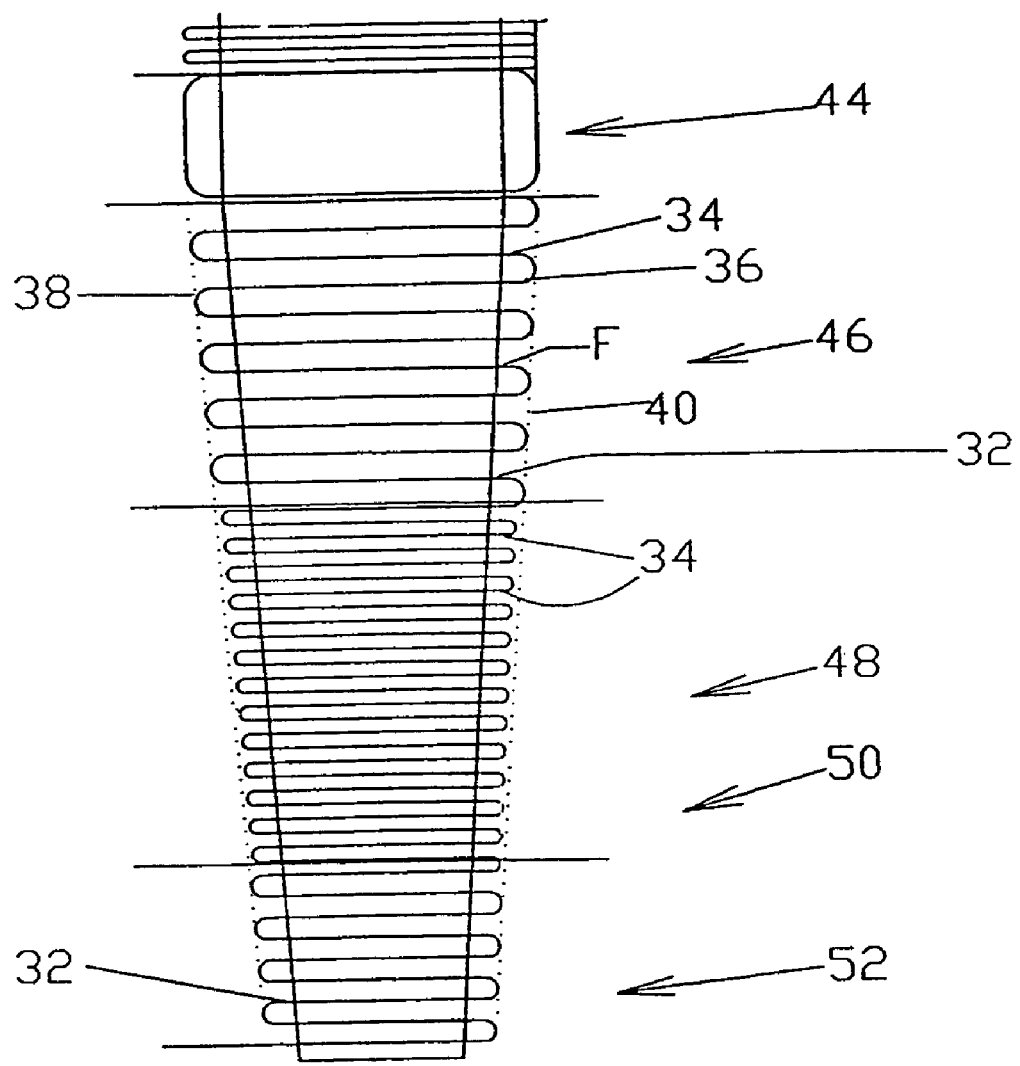
FIG. 5 is a schematic diagram of another embodiment of reinforced graft prior to rolling into a frusto-conical shape.

In the embodiment of FIG. 5, the reinforcing wire 32 is embroidered onto the sheet material 40 as a sinuous pattern which extends over the length of the sheet 40 between the spring elements provided by the wire 32. The sinuous pattern comprises a multiplicity of linear regions 34 which are mutually approximately parallel and which extend laterally of the sheet 40 between the side edges of the sheet. The spacing between these linear regions 34 is greater in the upper wider part of the sheet material 40 than in the narrower part. Adjacent linear regions 34 are joined together alternately by semi-circular bends 36, 38 disposed adjacent the side edges of the sheet 40.

When the sheet 40 having the reinforcement wire embroidered thereon is bent to form a tube, the wire 32, as in the embodiments of FIGS. 1, 2 and 4, is on the outside of the tube. The now-adjacent side edges of the sheet are stitched together to form a seam which is folded so as to lie inside or outside the tube so that adjacent bends 16, 18 on opposite sides of the seam can be secured together by knotting using ties.

Thus, in this embodiment, the linear regions 34 in the completed tube define a multiplicity of hoops around the tubular graft. These hoops are spaced apart longitudinally of the direction of extent of the tubular graft and thus allow the latter to be bent in a controlled manner without undue kinking at any specific location, thereby mitigating the risk of significant stenosis in use. The end of the tubular graft corresponding to the lower region illustrated in FIG. 5 is of smaller diameter and retains, in this example, a similar ratio of hoop spacing to graft diameter.

The pitch of the sinuous pattern is varied longitudinally of the sheet 40 so that the pitch is greatest in the section of the graft 34 that is to be subjected to the greatest degree of curvature. In section 42 there is a high density pitch to create a collar to hold the neck of the graft fully open and in firm contact with an artery wall. Section 44 is left unreinforced to provide an area for fixation of the graft to the artery wall with an additional fixation device (not shown).

Section 46 is of low density pitch where the graft is intended to traverse a relatively straight path through the centre of an aneurysm. Section 48 is a transition section with medium density pitch to avoid kinking at the transition to section 50 which is of a high density pitch. At section 50, the graft is required to pass through the most tortuous section of a common lilac artery. Section 52 is of medium density pitch to coincide with that portion of the graft which is intended to lie in the region of the artery which straightens into the external lilac artery. The optimum pitch for any section of the graft is a function of the expected degree of curvature and the diameter at that section.

The fabric used for the graft is standard fabric use in the art, for example micro-fine woven polyester. The wire may be of any suitable filamentary material, such as a nickel/titanium shape-memory alloy (SMA) material, a super-elastic shape-memory alloy material such as that sold as Nitinol. Substances other than shape-memory alloy could be used, the requirements for preferred embodiment being a material which can be deformed to assist insertion of the graft into an artery or other vessel or conduit and which can subsequently return to its un-deformed shape so as to open the graft once inserted.

The advantage of shape-memory alloy is that the graft can be compressed easily for insertion and then allowed to expand to its memorised shape as it heats up to body temperature.

For this purpose, the preferred embodiment uses an equi-atomic nickel/titanium alloy which is triggered at about blood temperature and which in a fully annealed condition is highly ductile. This condition is not typically used in medical devices which commonly employ "super elastic" material (sometimes referred to stress-induced martensitic (SIM) alloy). The use of a ductile alloy greatly eases handling during manufacture. Preferably, the ductile wire is mechanically polished before integration into the graft.

The preferred diameter of the wire is 0.2 mm to 0.3 mm, although any diameter between 0.15 mm and 0.5 mm can be used.

If the graft is provided with barbs, these need not be of shape-memory alloy.

The thread used to stitch the reinforcement wire to the fabric sheet is preferably a reduced friction coated yarn.

Figure 6A:
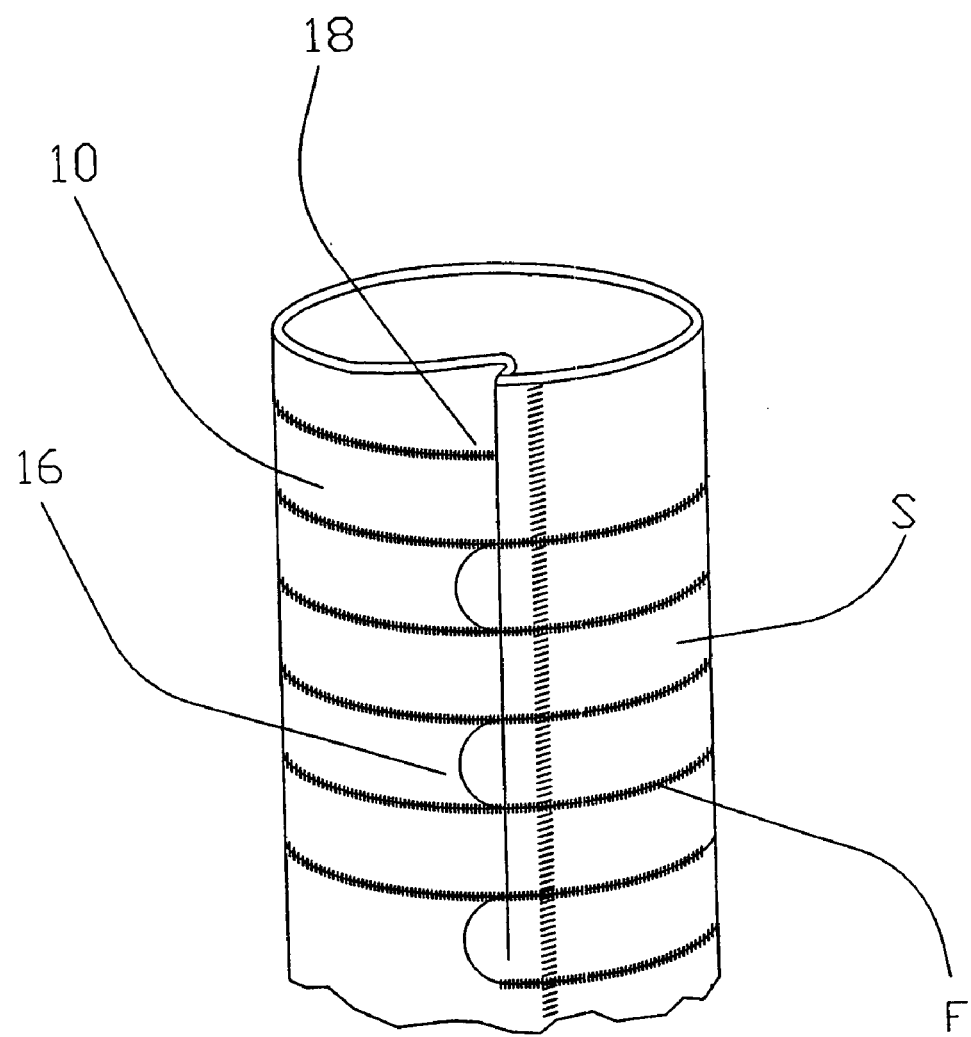
FIGS. 6a and 6b show two different methods of joining a reinforced graft into tubular form with both ends of a reinforcement rung opposing one another.
Figure 6B:
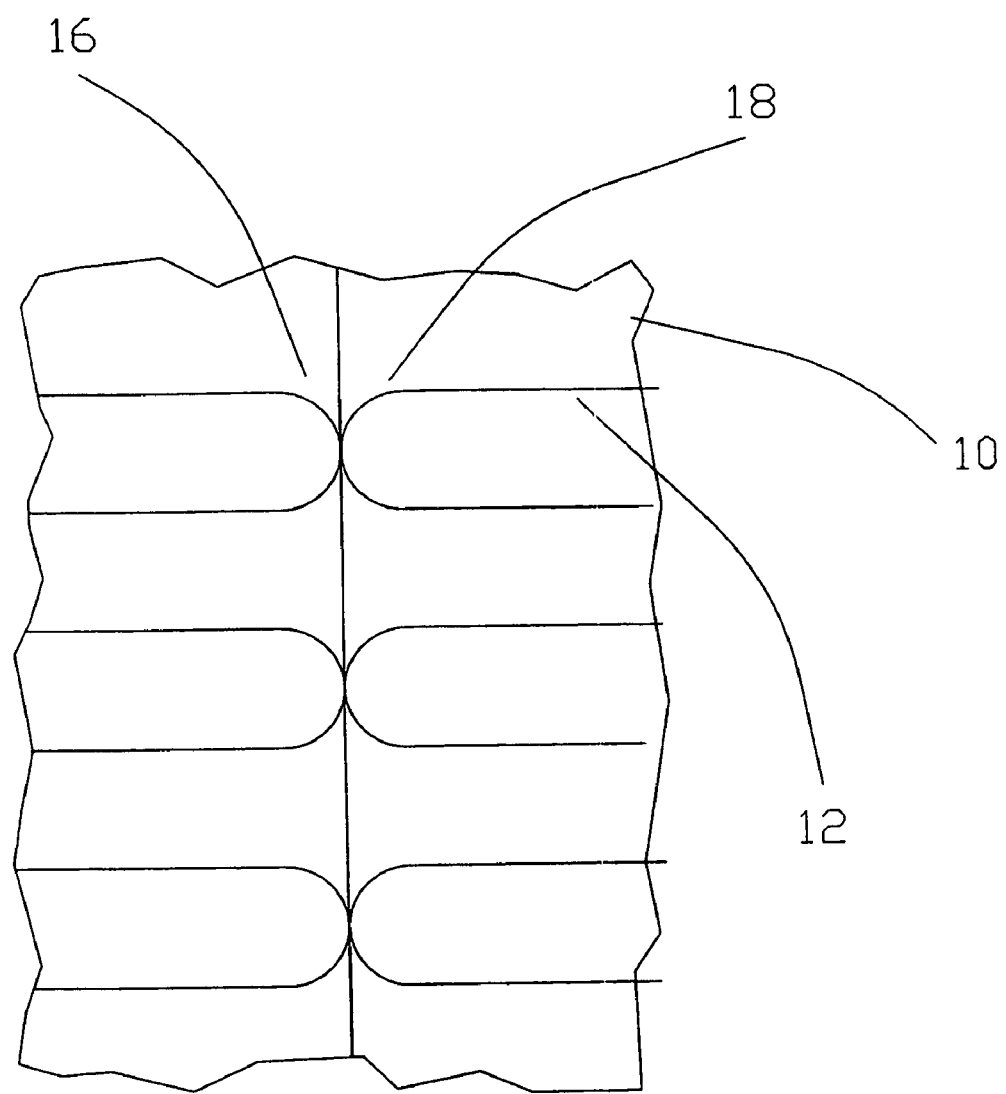
Figure 7:
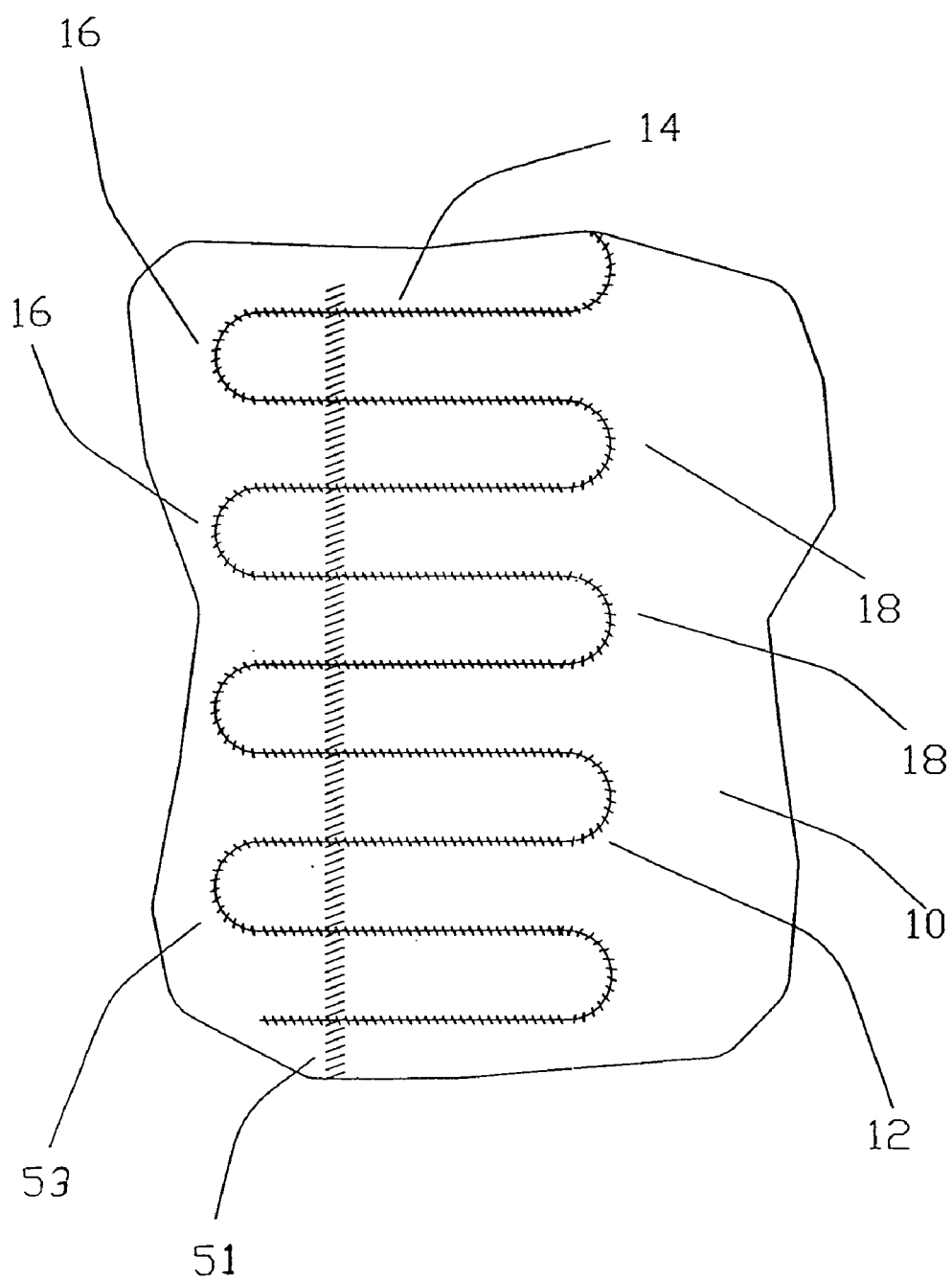
FIG. 7 is a schematic diagram showing a method of stitching a reinforcement ladder lattice.

The preferred method of producing the graft is now described, with reference to FIG. 7 in combination with FIGS. 3a, 3b, 6a and 6b.

As has been described with reference to the embodiments of FIGS. 1, 2, 4 and 5, the sheet material of appropriate shape is preferably laid substantially flat with a single wire of reinforcement material being laid on top of the sheet of fabric. For this purpose, the wire is preferably produced in a substantially planar configuration and, as can be seen in the Figures, can be said to have a sinuous or ladder pattern.

Referring to FIG. 7, a first stitch line 51 is produced close to one edge of the wire ladder 12. Once this line of stitches is produced, the wire 12 can be moved laterally across the sheet 10 for correct location. Once located correctly, the curved ends 16, 18 of the wire are stitched 53, prior to stitching of the substantially straight portions 14 of the ladder rungs.

Usually, shaped-memory alloy wire is heat treated in the shape which is to be its final form. On cooling, the wire is ductile and easily deformed but on warming to body temperature, the wire reverts to the form which it has been "taught". In the preferred embodiment, however, no such "teaching" is involved, apart from the planar shape of the wire as originally supplied. It has been found in practice that on heating the wire, when attached to the graft in the manner described, the graft forms a desired rigid cylindrical shape without the need for precise training of the wire. Moreover, such formation of the tubular graft causes it to be prestressed and therefore relatively stiffer than an un-stressed equivalent. This enables the use of wires of smaller diameter.

The ratio of the spaces between ladder rungs to the diameter of the graft is most preferably 1:3. A ratio of 1:2 has been found to work, with a ratio for the stiffer parts of the graft being preferably around 1:9. It has been found that a ratio of ladder rungs to diameter of 1:20 is also possible, sometimes benefiting from the use of a softer graft material.

FIG. 7 shows straight portions 14 of the wire 12 being stitched substantially continuously along their length. In order to allow for slight buckling of the graft to pass through catheters and to fit arterial curves, the stitches are preferably loose. This can be achieved by reducing stitch tension, increasing stitch size and/or using a reduced friction coated yarn. The preferred embodiment uses an increased stitch size and it has been found that a stitch size around three times the diameter of the wire is suitable although stitch sizes between six to nine times the diameter of the wire have also been used.

Another feature which can lead to different graft characteristics is the orientation of the wire rungs relative of the weft or warp of the fabric. More specifically, when the straight portion 14 of the wire 12 lie parallel to the weft or warp of the fabric sheet 10, the graft becomes substantially stable. On the other hand, when the straight portions 14 of the wire 12 are oriented so as to lie at an angle, for example 45°, to the weft or warp of the fabric sheet 10, the graft becomes more deformable. Alternatively or additionally, the fabric sheet 10 could be elasticated.

Stitching is preferably carried out by means of a computer controlled embroidery machine of the type particularly used to embroider insignia, badges and logos on uniforms, leisure wear and promotional garments. These machines have the advantage of being fast and providing reliable repeatability.

It is also envisaged that with computer controlled embroidery and by the design of the graft of the preferred embodiment, it would be possible to design specific grafts by CAD/CAM techniques, thereby considerably facilitating the production of custom implants.

However, manual stitching techniques can also be employed.

Once the reinforcement wire 12 is sewn to the fabric sheet 10, the sheet 10 is then rolled along its longitudinal axis to form a tube, with the opposing curved ends 16, 18 of the wire 12 moving so as to be located adjacent one another. Once rolled, the longitudinal edges of the sheet 10 are sewn together.

In FIGS. 3b and 6b, the edges of the sheet 10 are sewn such that the curved ends 16, 18 of the wire 12 do not overlap one another. On the other hand, in the embodiments of FIGS. 3a and 6a, the edges of the sheet 10 are stitched so as to overlap one another and such that the ends 16, 18 of the wire 12 also overlap.

In FIG. 3a, the ends 16, 18 interdigitate, whilst in FIG. 6a the ends 16, 18 overlap in substantial alignment.

As will be apparent in FIG. 3a, there are shown stitches 60, 62 which stitch together the overlapping ends 16, 18 of the wire 12. Similar stitches will be provided in the example of FIG. 6a. The advantage of stitching 60, 62 in the manner shown is that this ensures the graft has a substantially circular axial cross-section, with the stitches 60, 62 preventing deformation from the circular shape. Without such stitching, the force produced in seeking to return the wire 12 to its substantially flat shape causes the tube to adopt a pear-shape.

The examples of join shown in FIGS. 3b and 6b can be arranged nevertheless to ensure that the graft is substantially circular in axial cross-section by, for example, bending the ends 16, 18 out of the planar configuration at a radius which would be equivalent to the radius of the graft when rolled into its tubular form.

One feature of having the ends 16, 18 of the wire 12 overlap is that along the seam the graft exhibits a certain degree of longitudinal stiffness. When the ends 16, 18 do not overlap (for example abut one another) this longitudinal stiffness is not apparent. This can facilitate deployments which involve inversion of the section of the graft and can also facilitate an intra-operative adjustment in length of the graft by allowing the graft material between pairs of rungs to vary between being taut and buckled. An example of graft could have the loops interdigitating for the main body of the device and overlapping for the ends where the artery wall provides more natural support to the circular cross-section required from the graft and where an optional adjustment in length may be desirable.

Once set in its tubular form, the graft is substantially ready for use. Other elements may be attached to the graft, as described below.

In the preferred embodiments, the reinforcing wire 12 is located on different sides of the fabric sheet 10. More specifically, in the examples described above, the reinforcement wire 12 has been located on a single side of the fabric sheet 10, in use to be either on the outside or on the inside of the fabric tube once rolled.

However, it is sometimes preferred to have at some portions of the graft reinforcement wires on the outside of the graft and at other portions reinforcement wires on the inside of the graft. This can be achieved by using separate wires or by using a common wire which, during the placement process, it pushed through the fabric sheet 10 so as to be located, respectively, on one and on the other side of the sheet 10. Stitching can be achieved equally well with the wire on both sides of the fabric sheet 10.

A preferred embodiment has the wire on the inside of the graft at the ends of the graft, where optimum seal is required between the graft and the wall of an artery. In the centre portion of the graft, where it is desirable to minimise the potential disruption to the blood flow and maximise the anti-kinking support to the graft material, the wire is located on the outside of the graft tube.

In dependence upon the manner of manufacture of the graft, it may be advantageous to form the graft inside out, the thus formed graft then being everted to its correct configuration. Similarly, eversion could be deployed to facilitate insertion of the graft into an artery.

Figure 8:
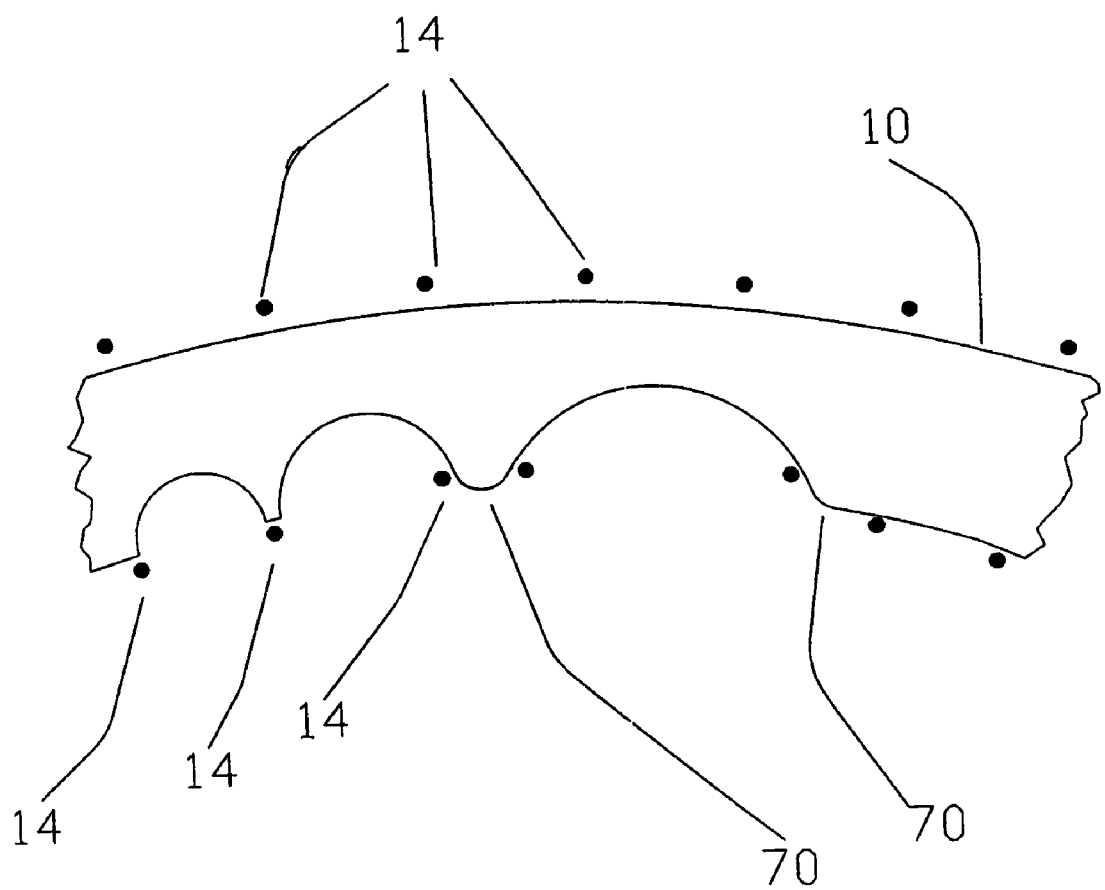
FIG. 8 is a schematic diagram showing the embodiment of reinforced graft of FIG. 1 in a flexed condition.

FIG. 8 is a cross-sectional view of the embodiment of graft of FIG. 1 which is bent into curved fashion. It can be seen that the graft sheet 10 is allowed to buckle 70 slightly so as to allow the graft to curve.

In the preferred embodiment, the entire graft can be wrapped around its own diameter in its longitudinal extent performing a tight curve without collapse or significant kinking.

Once the graft has been formed, it is then inserted into the artery of the patient in a manner known in the art.

In the embodiments which utilise a shape-memory alloy, the graft will be normally cooled to below the critical (trigger) temperature of the shape-memory alloy and compressed radially before it is inserted by the surgeon into position. This gives a compacted graft which may have a folded, star-like cross section which opens out after insertion into the body and heating to above the trigger temperature of the shape-memory alloy to return to a generally circular cross-section. When deployed within the arterial system, the graft should be sufficiently reduced so as not to over-expand, which could potentially damage the artery, but may have sufficient ability to increase in diameter to allow for any increase in size of the aneurysm after insertion. The graft may be located in a catheter or sleeve for insertion along the arterial system to the correct position. The provision of such a catheter or sleeve prevents expansion of the graft before it has been located in the desired position.

Typically, the graft will be introduced into the patient by means of a catheter which is cooled to allow the reinforcing wire of the implant to remain below body temperature and therefore ductile. The implant is drawn through the catheter to the implantation site by means of a pusher wire which is attached to the graft by means of wire or filamentary loops.

It is desirable to have a means of controlled release of the attachment loops so that for instance, a second pusher wire can be introduced next to the first pusher wire, and is attached to the proximal end of the graft. By pushing the second wire and puling the first wire, the implant can be everted.

Ideally, the entrance to the catheter is of an oval or stellate form so that the implant is crushed in a regular shape to have a smaller external diameter during implantation. Upon exiting the catheter into the blood stream the SMA wire of the graft is warmed and adopts a straighter shape similar to that originally formed in the implant.

Before describing other elements which can be formed on the graft of the embodiments described above, further embodiments of graft are described.

Figure 9:
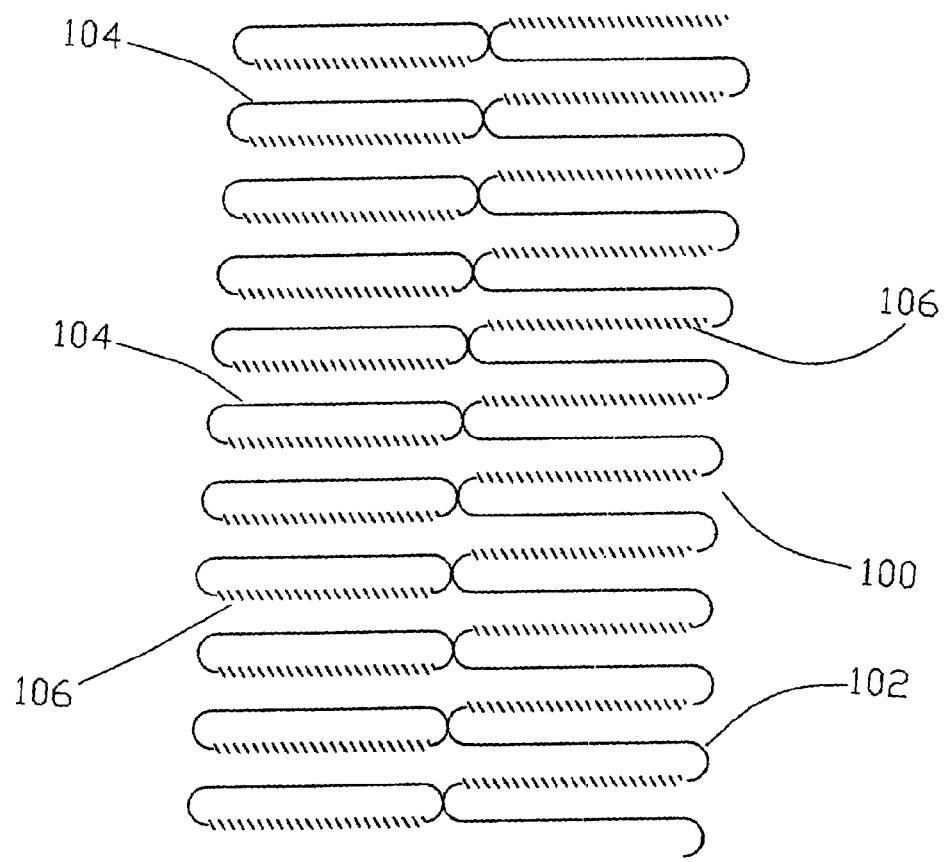
FIG. 9 is a schematic diagram of another embodiment of reinforced graft prior to rolling into a tubular shape.
Figure 10:
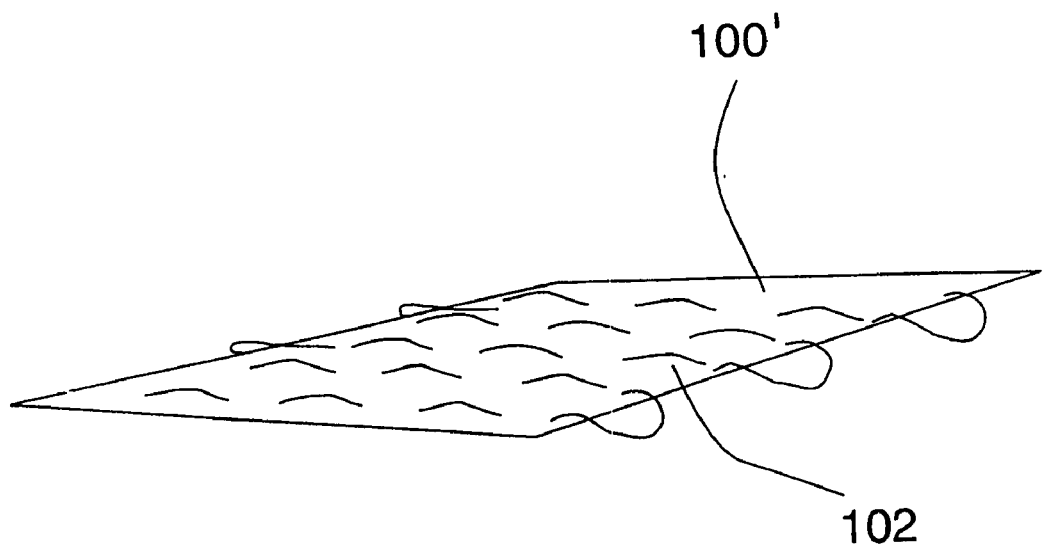
FIG. 10 is a perspective view of another embodiment of reinforced graft showing a wire stitched or woven through a sheet of graft fabric material, prior to rolling.

With reference to FIG. 9, a wire 102 is located on a sheet of fabric 100 such that some portions 104 of the wire are located above the sheet 100, as seen in FIG. 9 and other portions 106 are located below the sheet 100. This is achieved by sequential feeding of one end of the wire 102 into and out of the sheet 100 to provide the pattern shown. The specific pattern shown in FIG. 9 provides two stiffness lines in the longitudinal direction of the graft. In FIG. 10, the wire 102 can be seen threaded into and out of sheet 100'.

Figure 11:
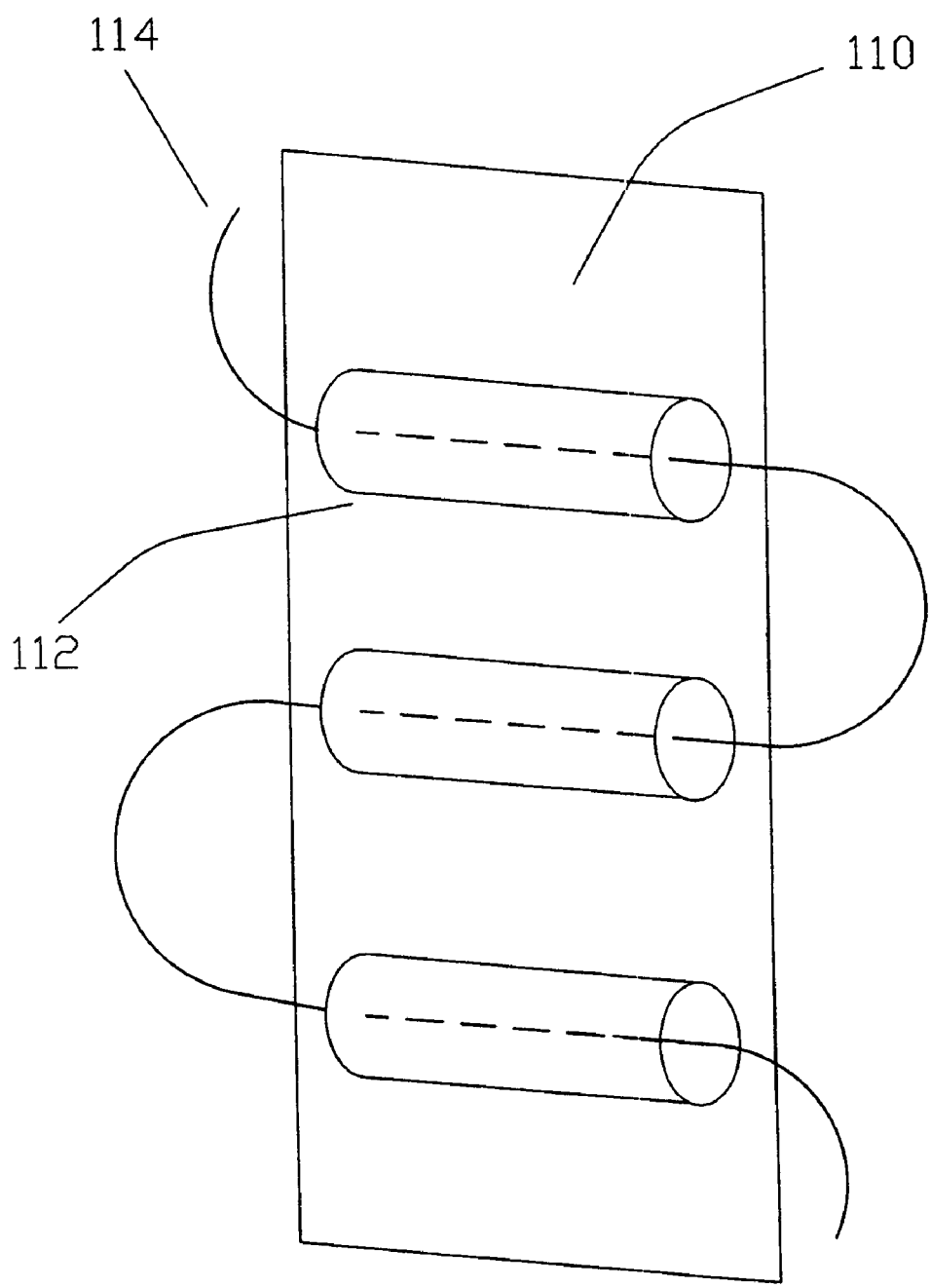
FIG. 11 is a perspective view of another embodiment of reinforced graft.

In FIG. 11, the sheet of graft fabric 110 is provided with a plurality of transversely-extending pockets 112 through which a wire 114 can be threaded. The pockets 112 provide the wire 114 its required shape.

Figure 12:
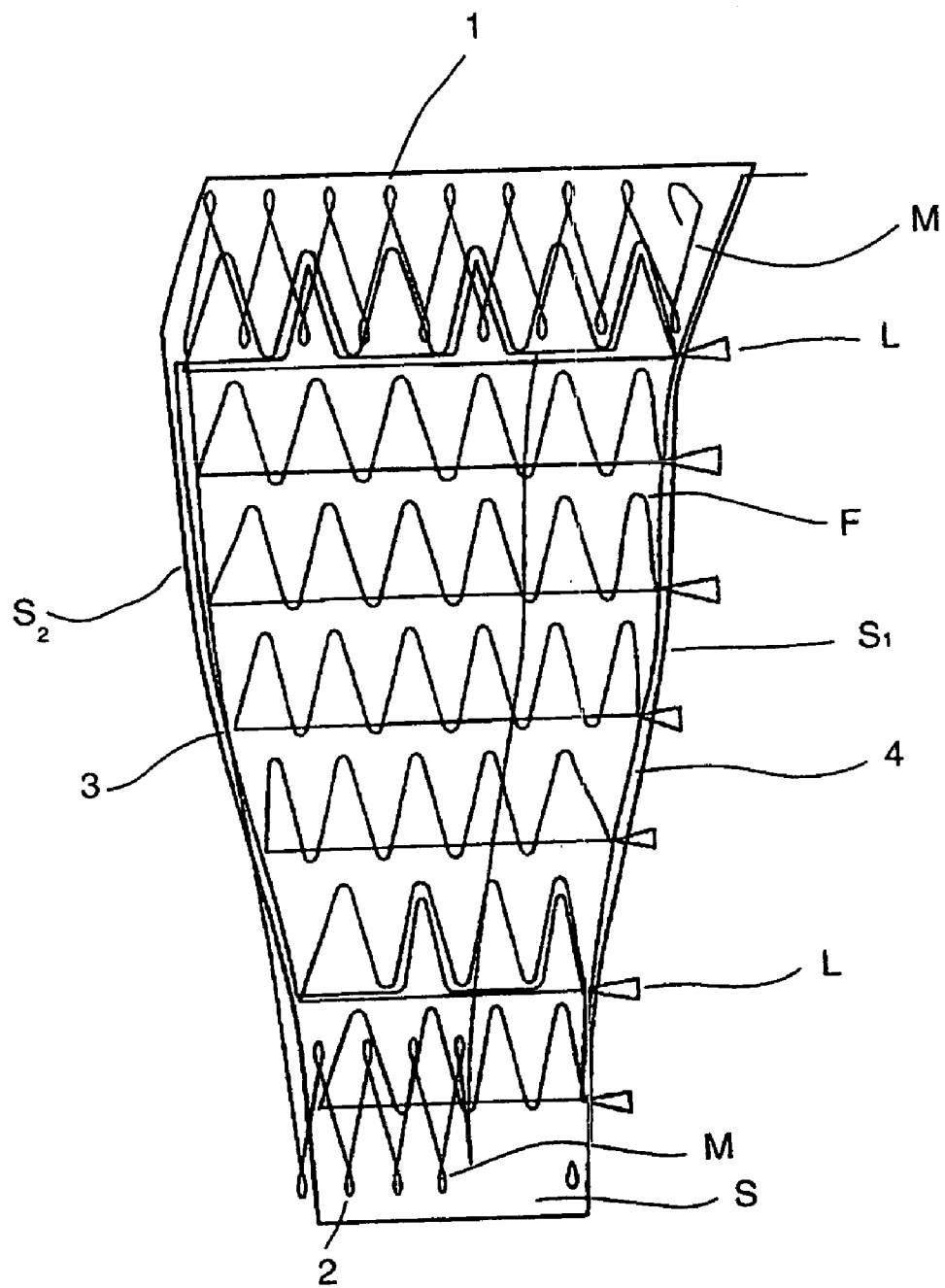
FIGS. 12 to 22 are schematic diagrams of other embodiments of reinforced graft.

In FIG. 12, a woven polyester microfibre sheet S has opposite side edges S1 and S2 tapering inwardly from top to bottom as viewed in FIG. 12 and is shaped so as to enable a tubular graft to be formed which tapers from a relatively wide diameter at one end to a relatively narrow diameter at the other end. The precise shape and size of the sheet S is determined according to the particular configuration of the aortic artery into which the tubular graft is to be fitted.

The sheet S has filamentary reinforcing material F stitched to one surface thereof by means of a computer controlled embroidery machine. The filamentary reinforcing material F is preferably a single filament which is secured to the sheet S so as to define a multiplicity of zig-zag patterns extending laterally of the sheet S between the side edges S1 and S2. The zig-zag patterns are spaced apart longitudinally of the sheet S over substantially the whole of the length of the latter.

The embroidery operation to form the filamentary reinforcing material F to the required shape also defines a series of loops L which project laterally beyond the side edge S1 of the sheet S. The sheet S is also subjected to a further embroidery operation in which a length of spring material M is used to form spring elements at the top and bottom. Each of these springs elements is defined by a zig-zag pattern extending across the sheet S. In forming the zig-zag pattern, the filamentary spring material is looped over at locations typically indicated by reference numerals 1 and 2.

Extending along the side edges S1 and S2 of the sheet are reinforcements 3 and 4 which provide longitudinal stiff pillars imparting lengthwise stiffness and column strength to the graft to prevent it buckling during insertion. The pillars 3 are defined by portions of the spring material M, while the pillar 4 is provided by regions of the filamentary reinforcing material F.

After the structure described above with reference to FIG. 12 has been produced, the sheet material S is folded into tubular form with the side edges S1 and S2 adjacent. These are then stitched together to form a seam and the loops L are secured by suture material to the now-adjacent opposite portions of the respective zig-zag patterns embroidered on to the sheet material S.

The loops at 1 and 2 enhance the properties of the spring.

Figure 13:
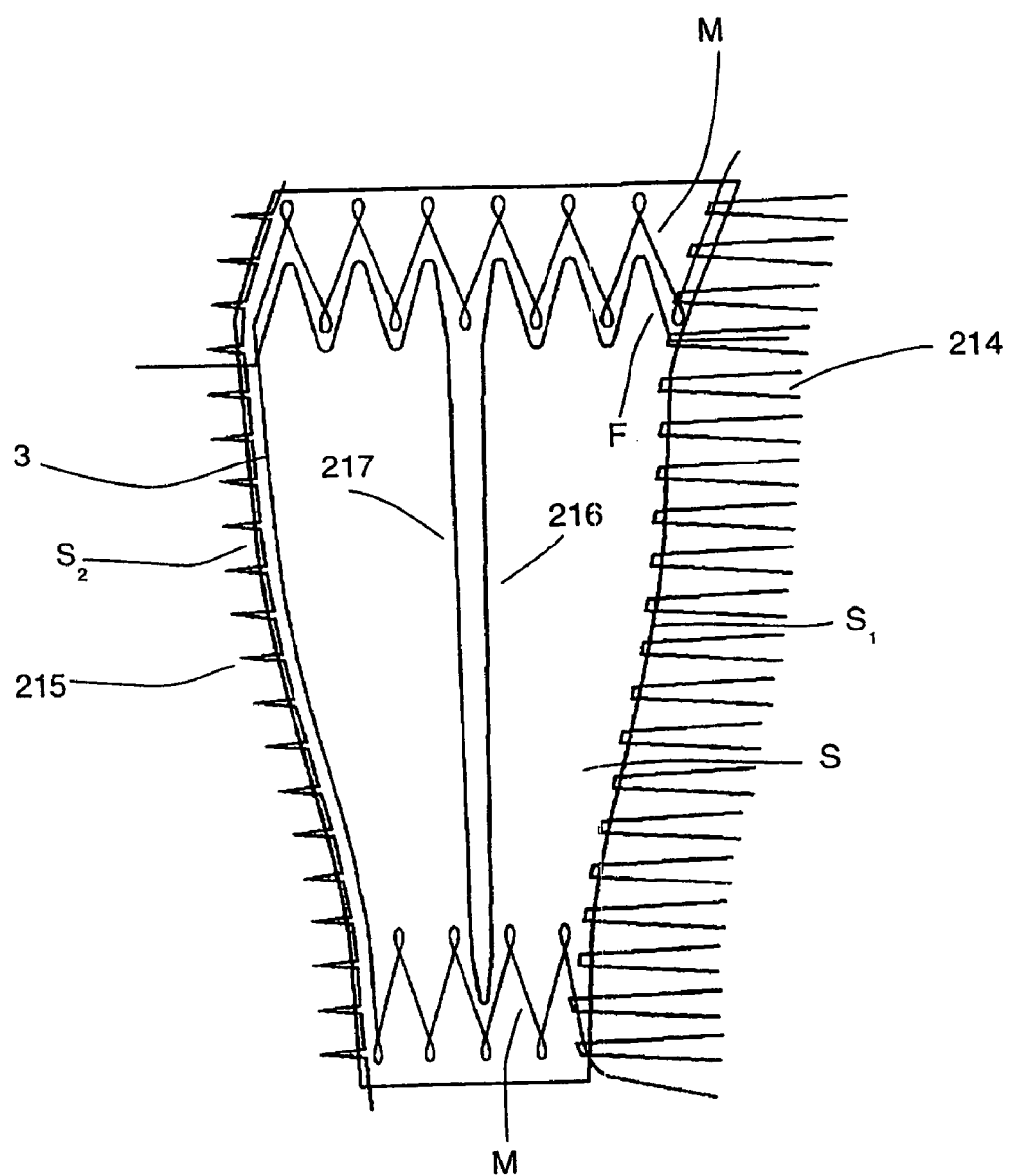

In FIG. 13, the graft is formed with ties 214 which are engagable with respective loops 215 when sheet material S is formed into a tubular shape. In this embodiment, further longitudinal stiffeners 216 and 217 are provided approximately midway between side edges S1 and S2. The ties 214 are knotted to the respective loops 215 to retain the tubular form of the graft.

Figure 14:
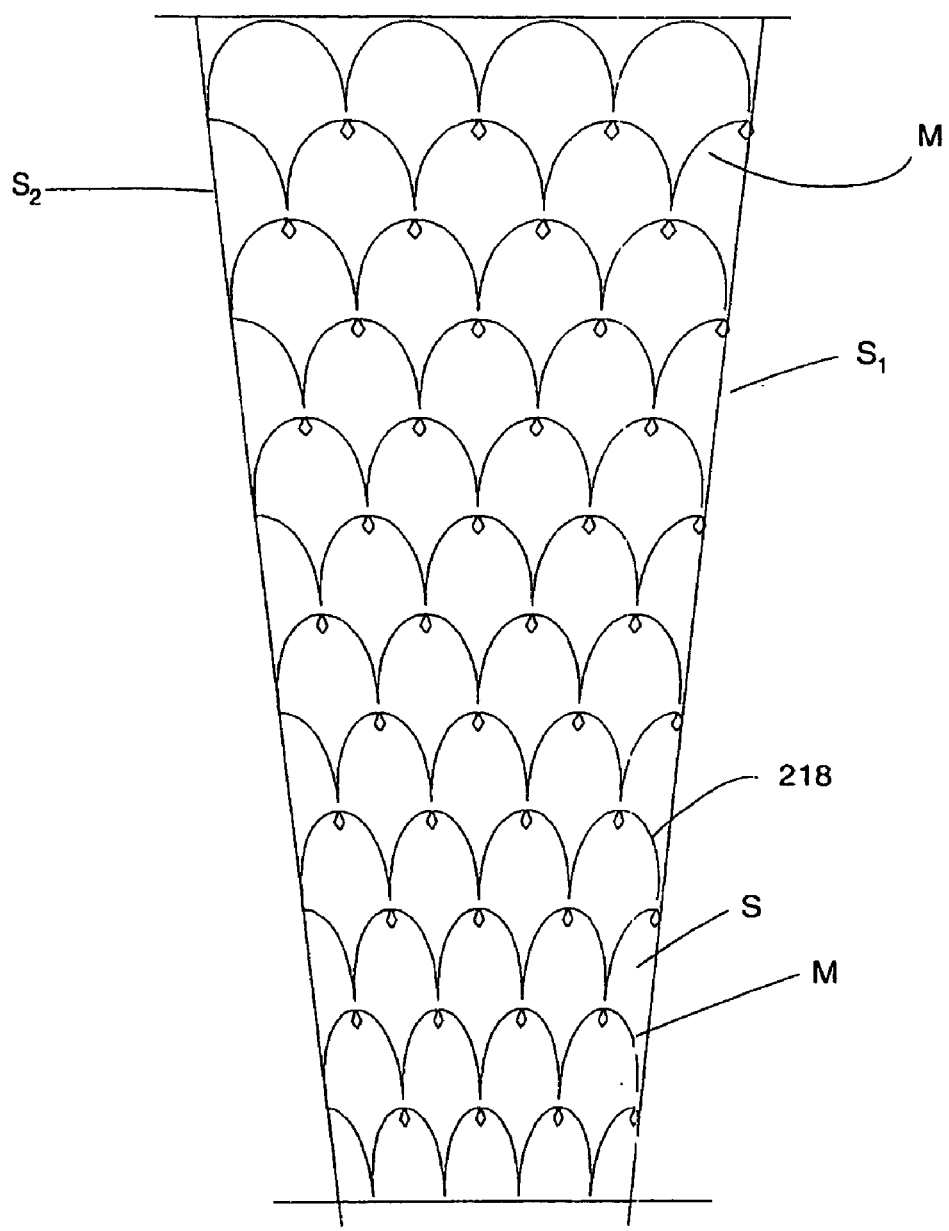

In FIG. 14, elementary spring material M is embroidered onto sheet S to form a series of bends 218 arranged in a fish scale pattern.

Figure 15:
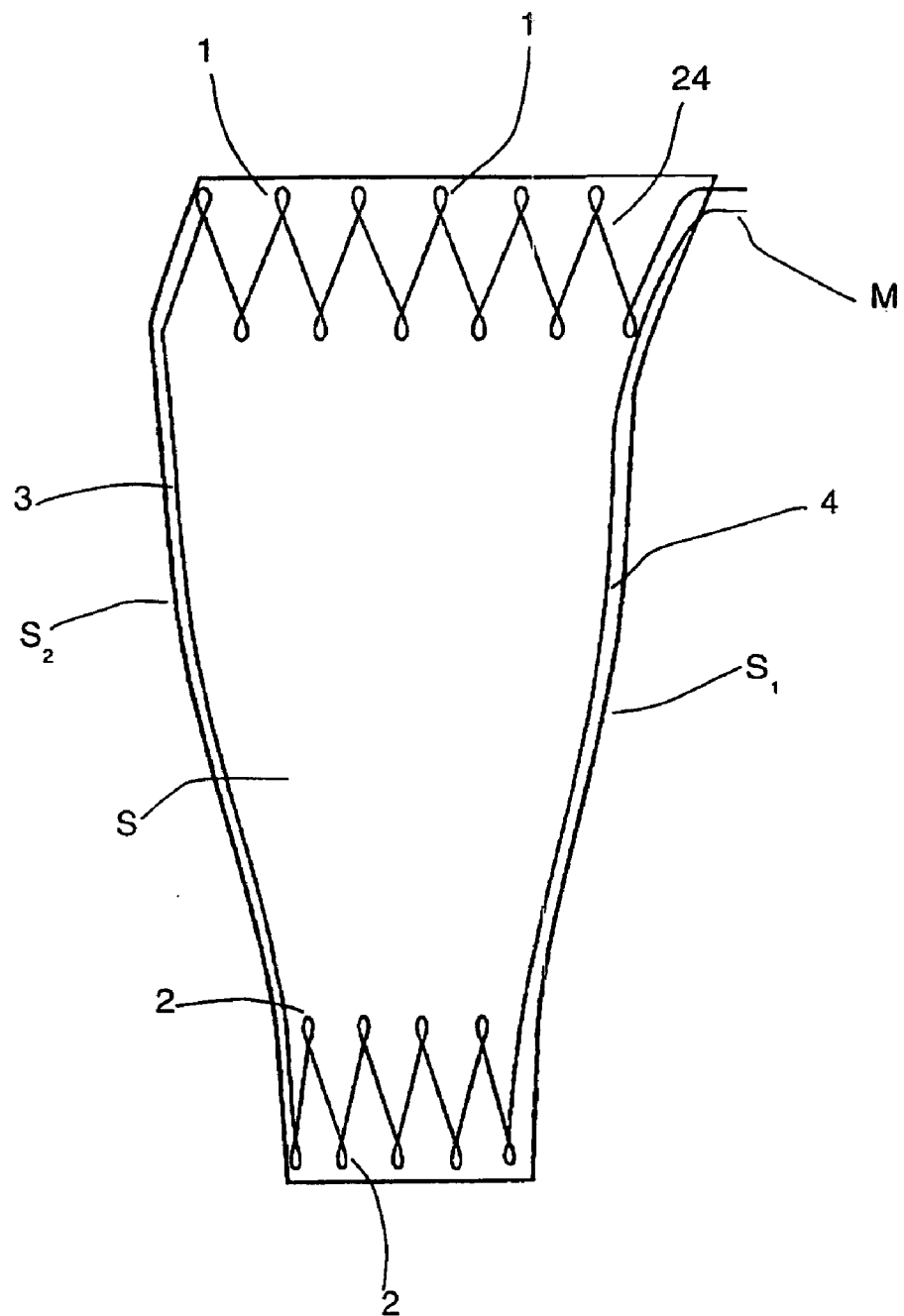

In FIG. 15, there is illustrated another pattern for forming the spring elements at opposite ends of the graft using elongate spring material M. The arrangement is similar to that of FIG. 12, but the path of the embroidery machine is different.

Figure 16:
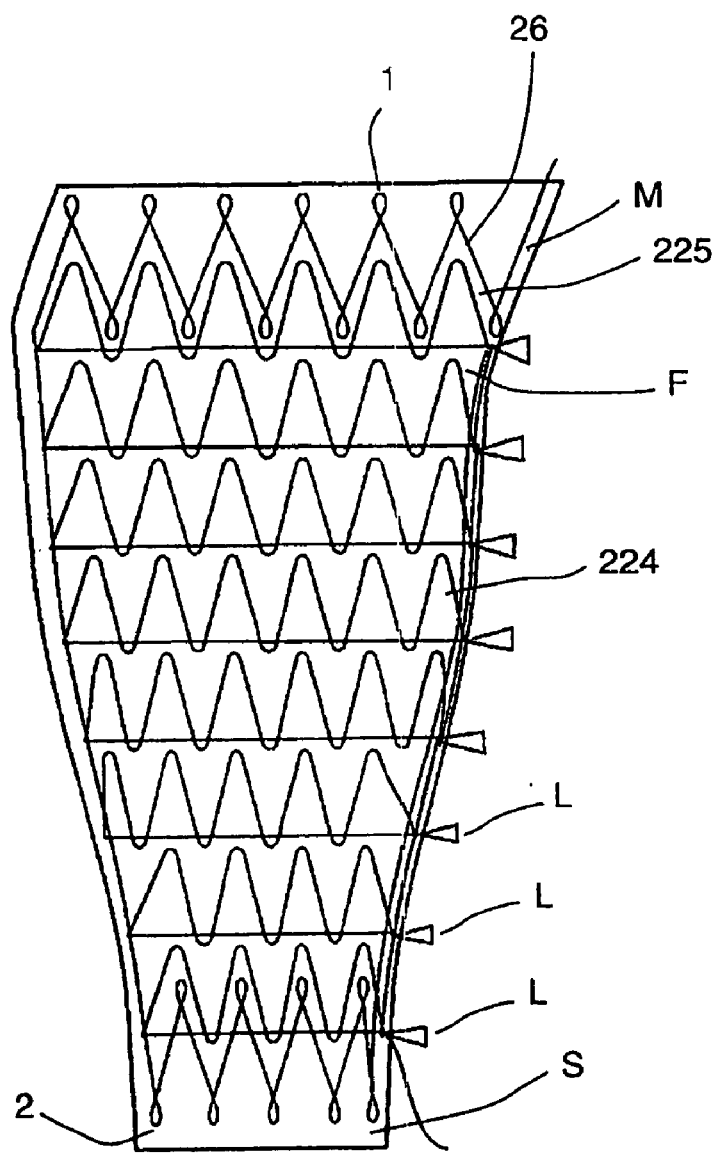
Figure 17:
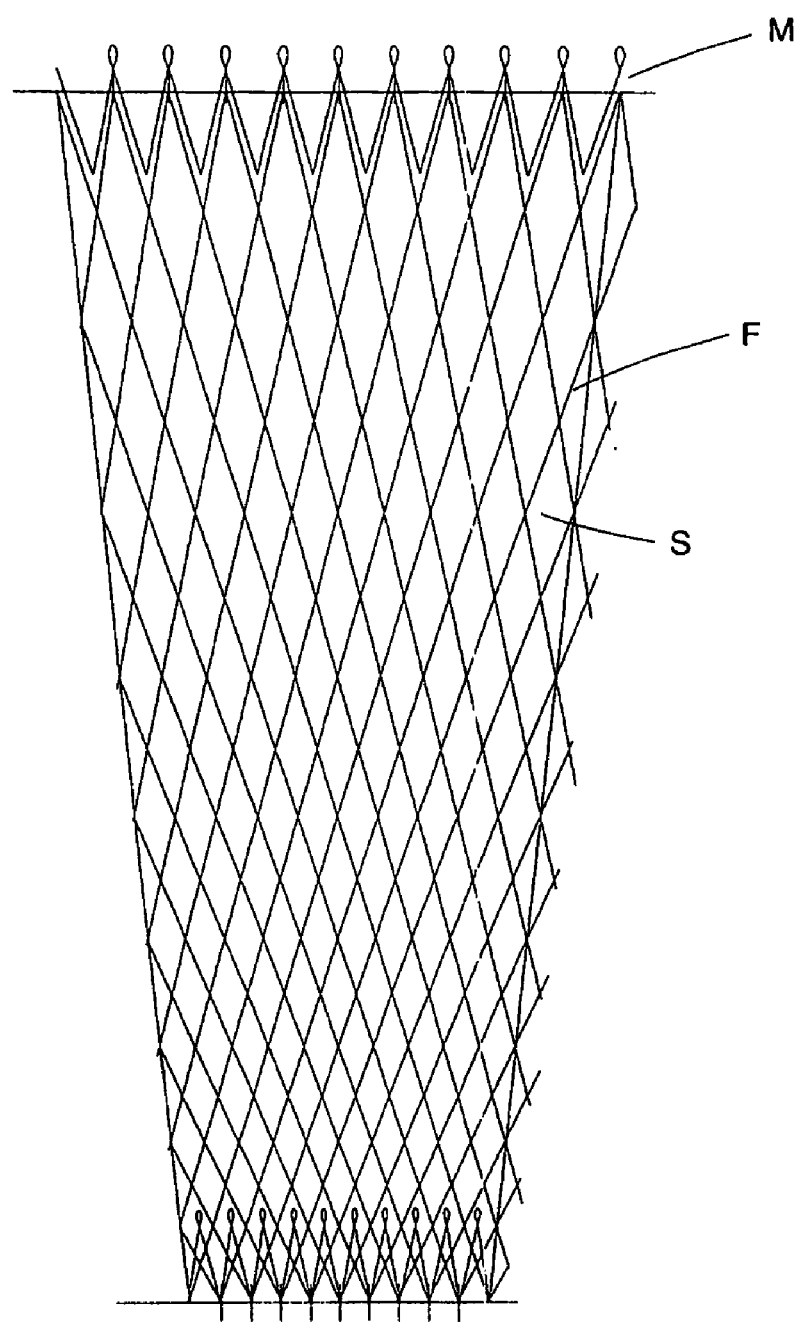
Figure 18:
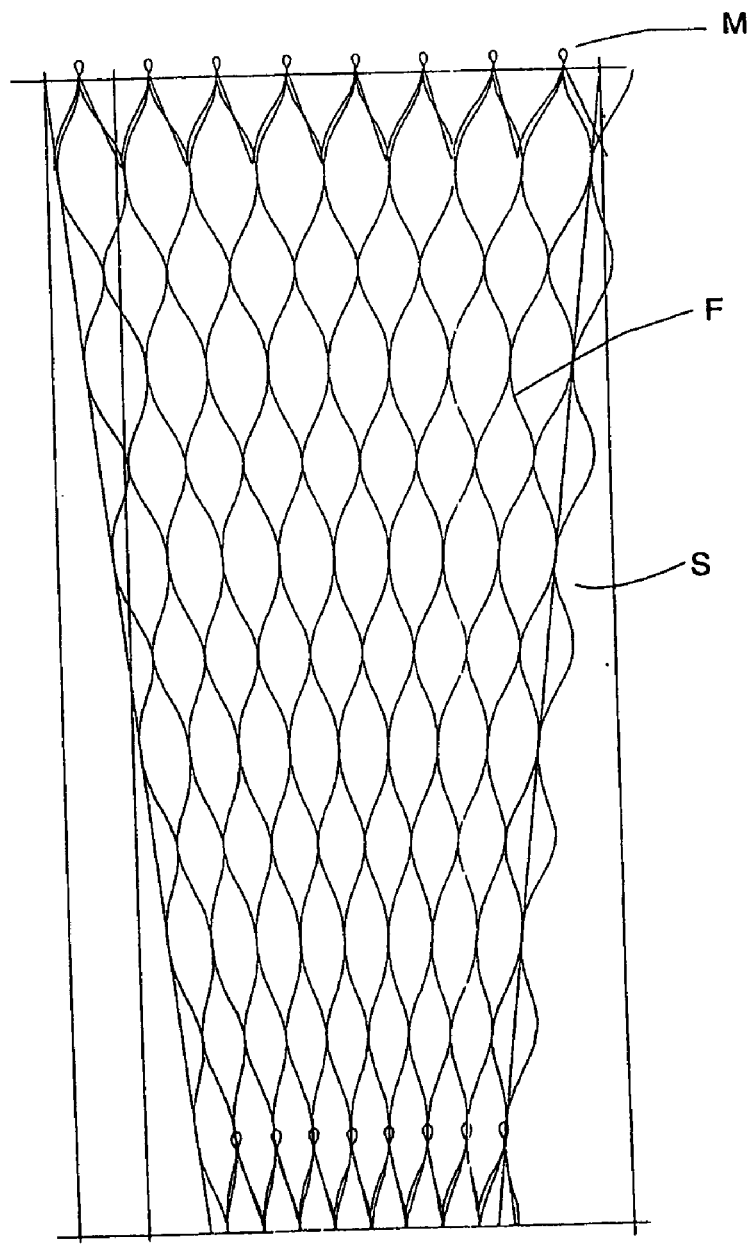
Figure 19:
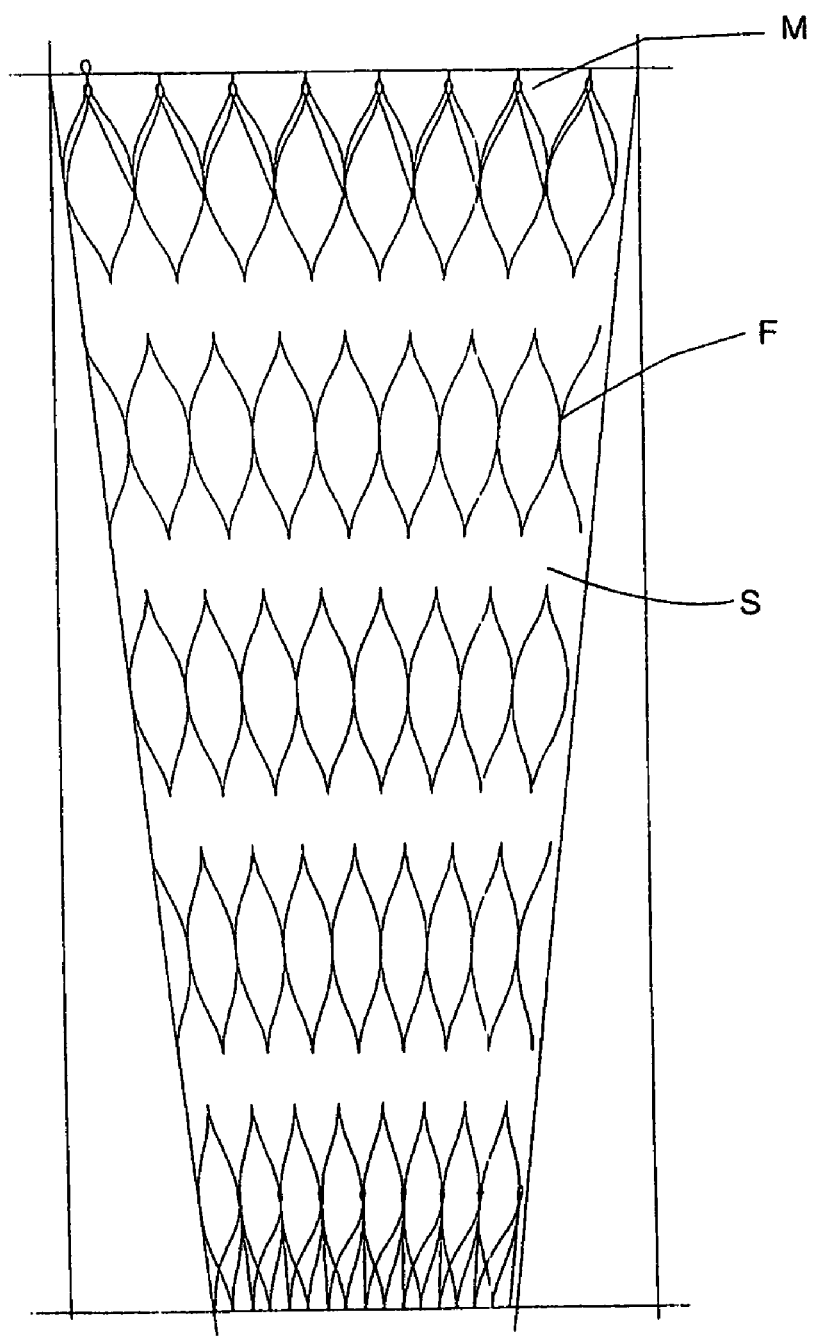
Figure 20:
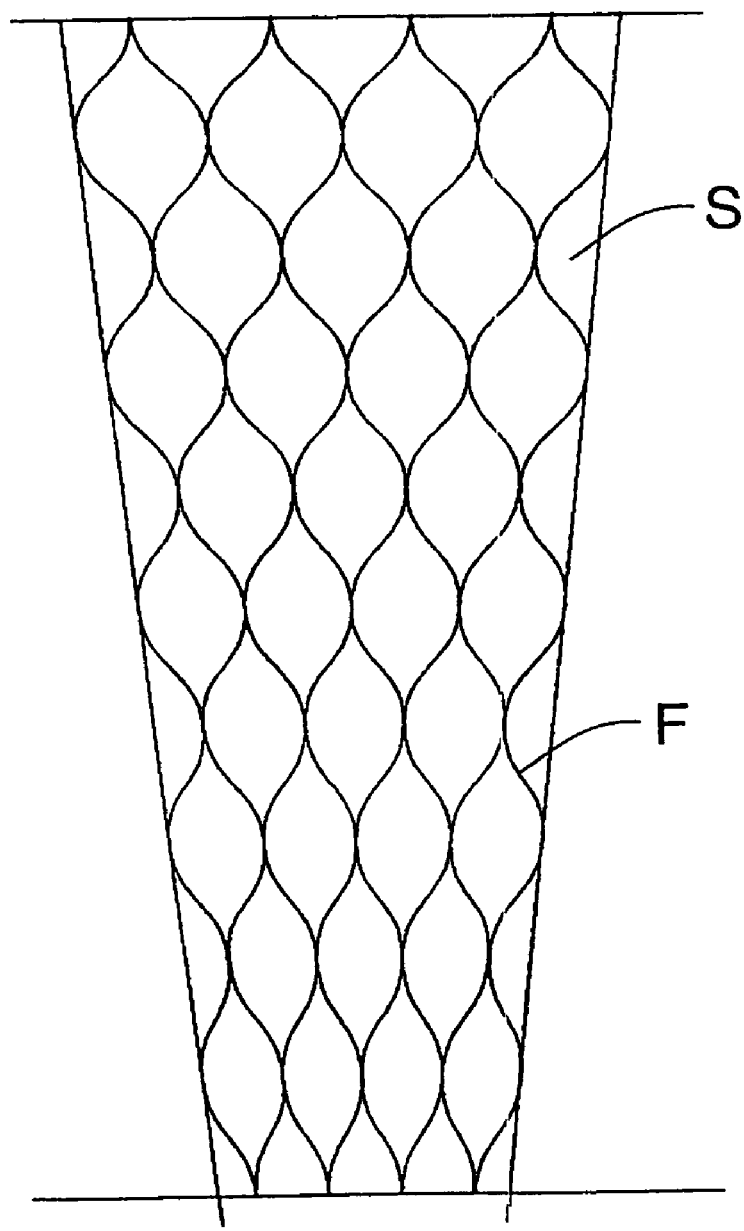
Figure 21:
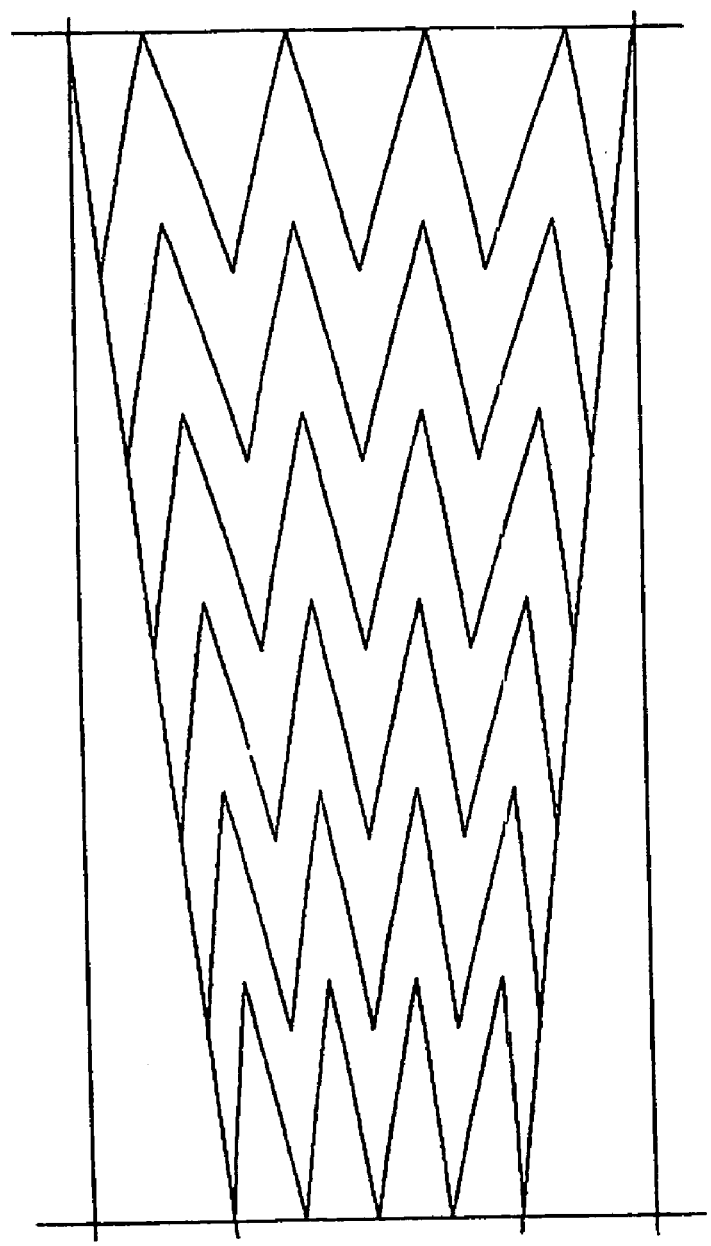
Figure 22:
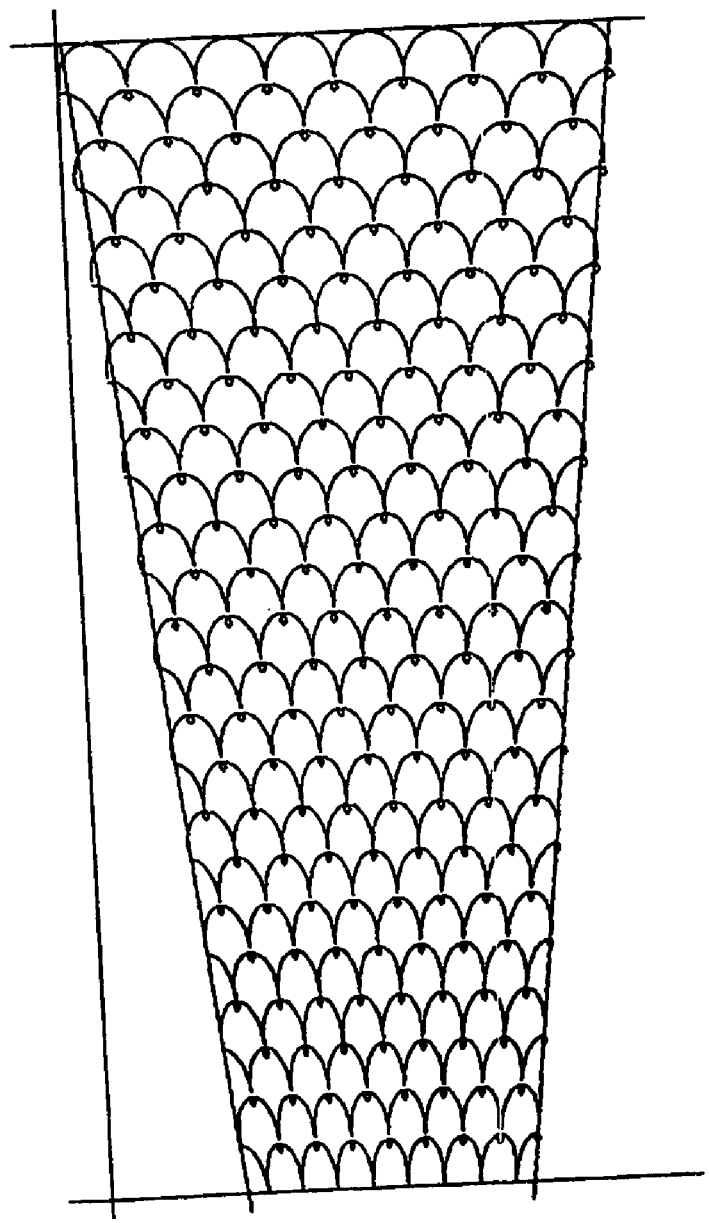

FIG. 16 shows an arrangement also similar to that of FIG. 12. Pattern 224 of the filamentary reinforcing material F is intermittent down the length of the graft to provide more flexibility. Retention hooks are shown at 225 which assist in retaining the graft in position in the artery in which it is fitted in use. The spring elements at the top and bottom of the graft are defined by the spring material M, and the small loops 1 and 2 are used to assist attachment of these to the sheet S.

FIGS. 17 to 22 show alternative patterns of the filamentary reinforcing material which can also be stitched at selected locations using a computer-aided embroidery machine onto the sheet S in order to provide columnar stiffness combined with radial springiness to hold the lumen open. At the top and bottom of the sheet S are shown looped hook wire arrangements acting to secure the graft in place.

The materials used for reinforcing in the above described embodiments may be any bio-compatible materials suitable for implantation, including nylon, polyester, silk, polyglycolic acid, polylactic acid and metallic wire. The use of monofilament polyester and super-elastic or shape-memory metals alone or in combination is preferred. The use of a super elastic, shape-memory alloy such as Nitinol allows the device to be self-expanding and does not require the use of an additional device (such as a balloon catheter) to expand the generally cylindrical shape from a compressed condition to an extended condition.

Additional elements for the embodiments of graft described above are now mentioned.

The device may be retained in the required position within the artery by use of a multiplicity of retaining bristles or barbs formed from suitably rigid metallic or polymeric material. These barbs may be arranged to protrude a sufficient distance from the external surface of the tubular graft and when provided in sufficient numbers they will engage within or through the wall of the blood vessel such as to resist movement of the graft under the force exerted by the flow of blood there through.

Figure 23A:
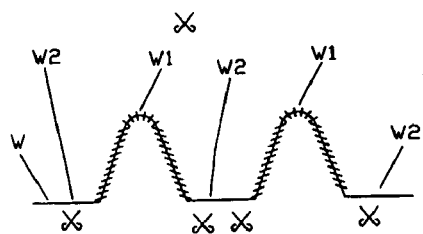
FIGS. 23a to 23f are schematic diagrams showing how barbs can be formed.
Figure 23A:
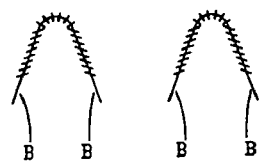

FIGS. 23a to 23f show various arrangements for producing bristles or barbs on the outer surface of the graft at the upstream end thereof relative to the direction of flow of blood therethrough. In FIG. 23a shape-memory alloy wire W is attached to the sheet S (not illustrated in FIG. 23) by stitching the wire using a computer-controlled embroidering machine over spaced bends W1 in the wire W. These spaced bends W1 are spaced apart around the periphery of the tubular graft and are interconnected by intervening regions W2 which are left free, i.e. are not attached by stitching to the sheet S.

Cutting of the wire W at these regions W2 as indicated schematically by the scissors in FIG. 23a results in the formation B in the completed graft. These bristles B point generally in the direction of blood flow through the graft and act as barbs which dig into the wall of the artery to prevent the flow of blood in the aorta, or other forces such as patient movement, from dislodging the graft from its placed position.

Figure 23B:
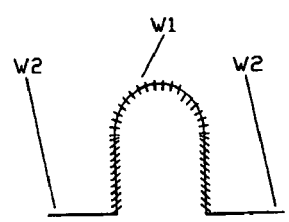
Figure 23B:

As can be seen from FIG. 23b at 180° bend W1 will result in the bristles B projecting parallel to the longitudinal axis of the graft. This is optimum for resisting the main force of the blood flow.

Figure 23C:
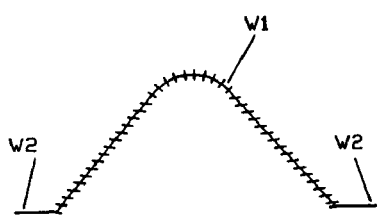
Figure 23C:
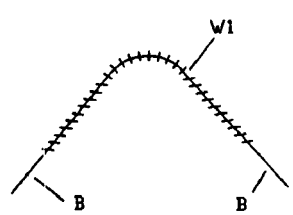
Figure 23D:
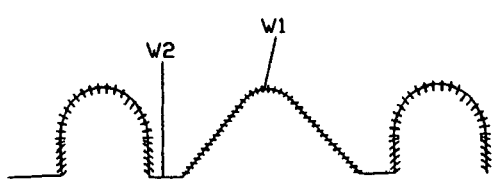
Figure 23D:
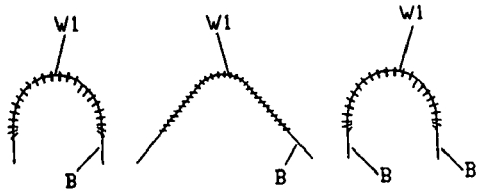

As indicated in FIG. 23c, bends W1 with an angle of less than 180° will result in the bristles B extending at an angle to the longitudinal axis of the graft. This configuration is optimum for resisting torsional forces acting on the graft.

As shown in FIG. 23b 180° Bends W1 may alternate with bends of an angle less than 180° to produce combined effects.

Figure 23E:
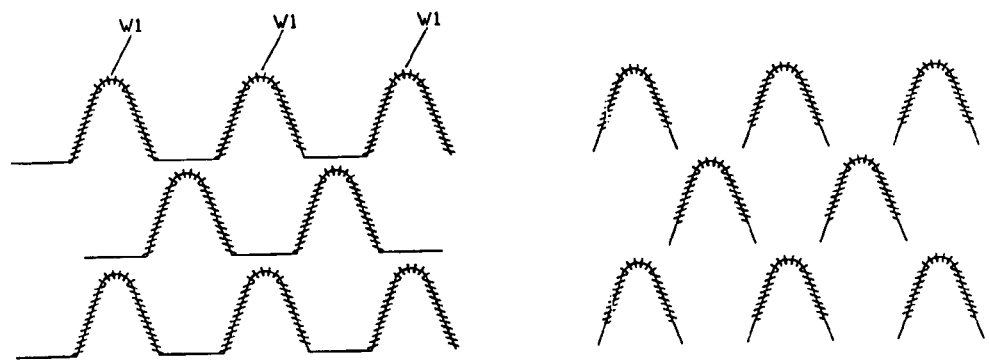

As shown in FIG. 23e there are three rows of barbs arranged in a staggered formation on the external surface of the graft such that there is an optimal variation in the direction of the extent of the bristles B to ensure that a mechanical lock with the wall of the artery is ensured irrespective of the lack of uniformity that is commonly found in arteries.

Figure 23F:
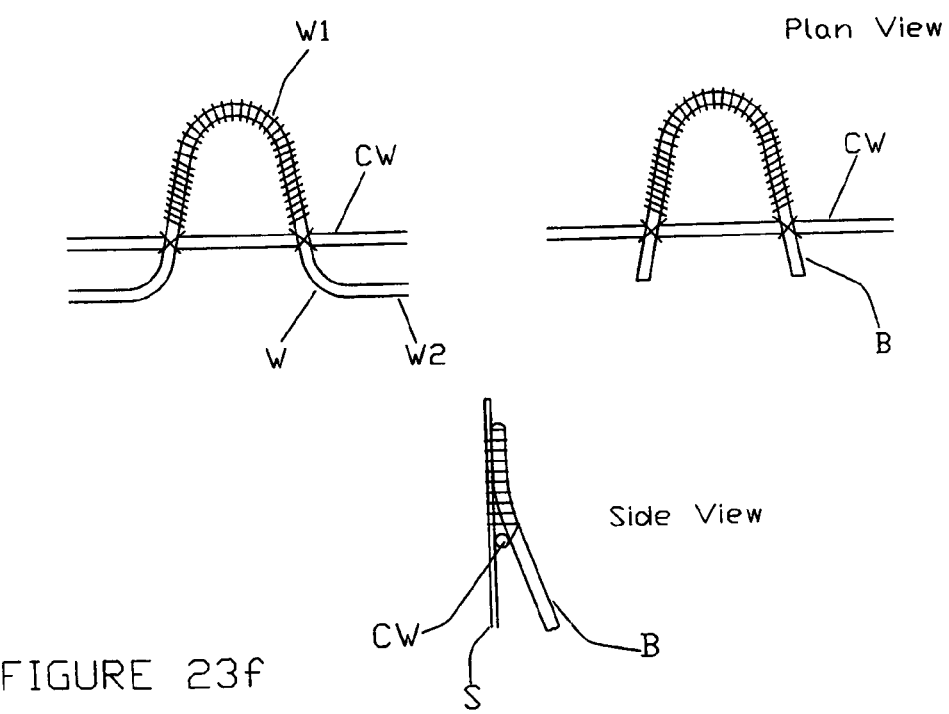

In FIG. 23f there is shown an arrangement where the wire W forming the bends W1 overlies a circumferential wire CW so that the latter is disposed in the region of the junction between the bends W1 and the intervening regions W2. The result of this is that, after cutting at the regions W2, the bristles B protrude at a definite angle from the surface of the sheet S.

Additionally, further stitching may be utilised in the region where the wire W crosses over the circumferential wire CW so as to provide additional anchorage or the bristles B at the points where these bristles protrude from the wall of the tubular graft.

The preferred embodiments also provide for the attachment of radio-opaque elements to the sheet of graft material. The elements are possibly embroidered onto the sheet of fabric. The preferred radio-opaque element is a fine wire embroidered in a pattern to provide calibrated deformations along its length to provide a radio-opaque length measurement along the longitudinal axis of the graft.

In an alternative embodiment, the radio-opaque elements provide indications of "left", "right", "anterior" and/or "posterior" and may, for example, be in the form of letters designating the first letter of each of these position terms.

In the case of a radio-opaque element, this could be a tantalum or other high molecular number element (opaque) wire embroidered onto the sheet of fabric. Alternatively, the radio-opaque markers could be a radio-opaque ink printed on the fabric, pellets or a sheet of material embroidered over the fabric sheet.

Figure 25:
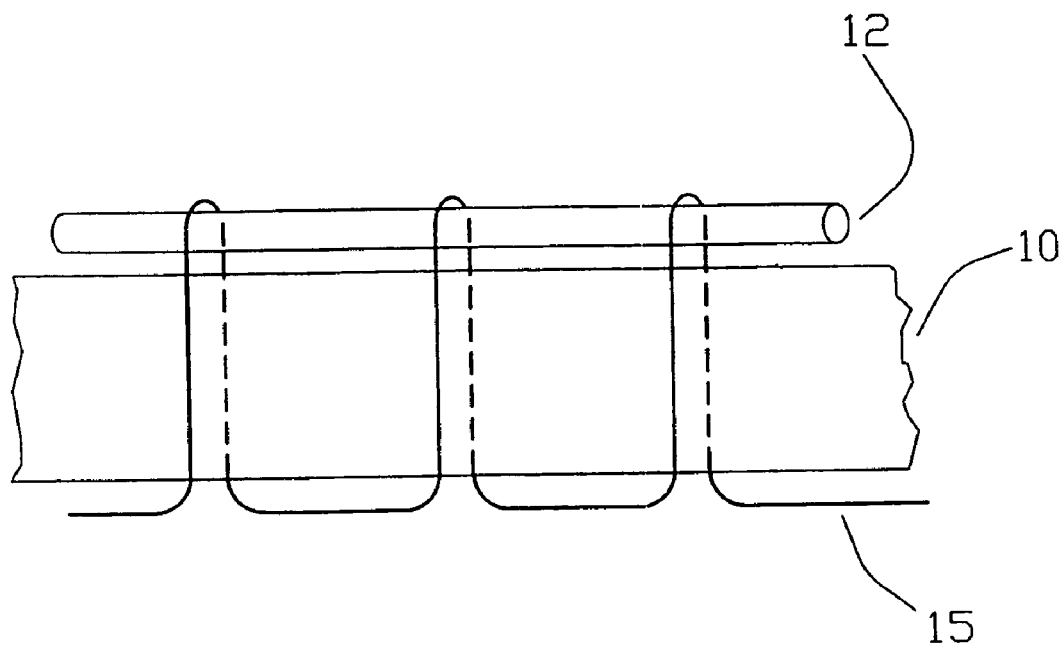
FIG. 25 is a schematic view of a reinforcement wire, barb or radio-opaque element sewn by a sewing machine to a fabric sheet.

The opaque markers, and indeed the reinforcement wire 15" itself or the barbs could be provided on a sewing machine bobbin to be placed on the fabric sheet 10" in a lock-stitch 15, as shown in FIG. 25.

Figures 24A, 24B:
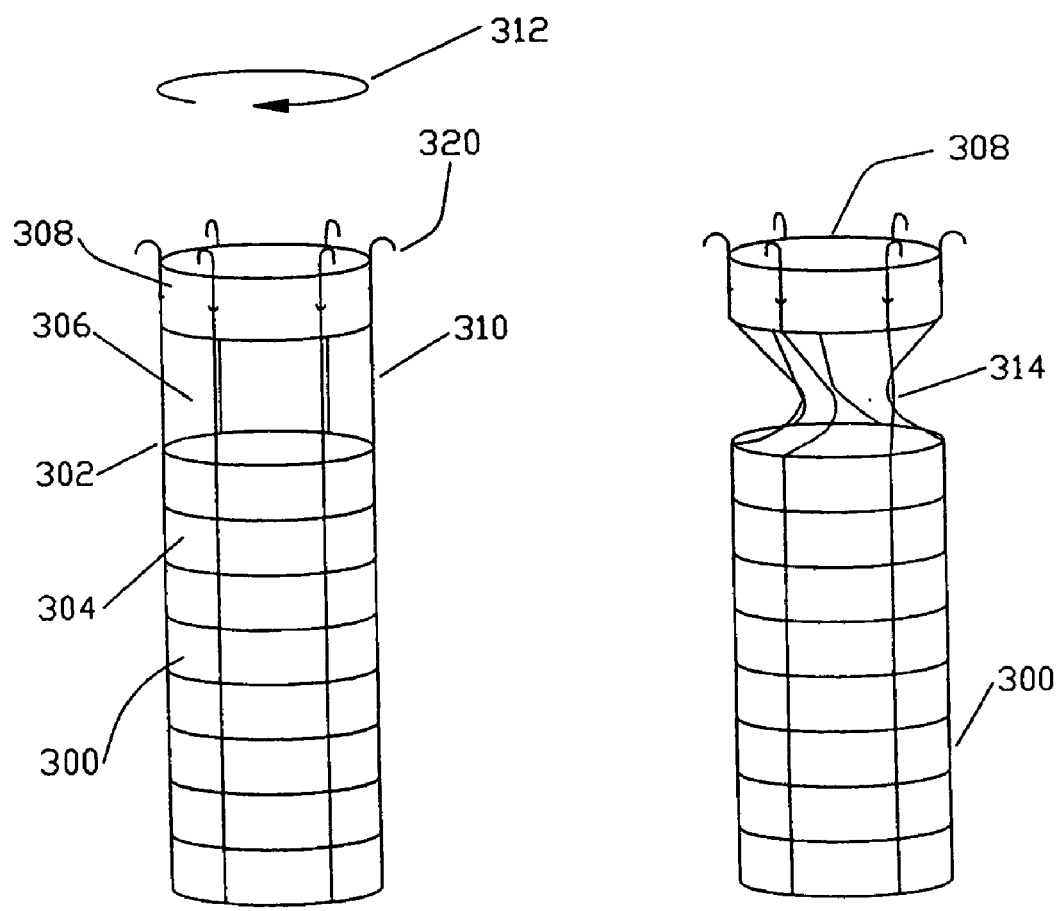
FIGS. 24a and 24b show another embodiment of reinforced graft.

In FIG. 24a is provided an example of graft 300 formed in accordance with any of the above-described embodiments and which has at one of its ends 302 a region 306 not covered by graft fabric 304. Beyond region 306, there is a small annulus 308 of graft material. Between the annulus 308 and the graft 300 there is provided a plurality of struts 310 of shape-memory alloy connecting the graft 300 to the annulus 308. The location 306 allows the graft 300 to be placed between two arteries.

The advantage of the structure shown in FIG. 24a is that the annulus 308 can be rotated, for example in the direction shown in the arrow 312, such that the structure 310 twists to a neck 314 as seen in FIG. 24b. A loose connection between the struts 310 and the annulus 308 assists in this generation of the neck 314. In its twisted shape, the neck 314 can be tied providing a very flexible leading end of the graft 300 by means of the mobility of the annulus 308.

It can be seen in FIGS. 24a and 24b that the struts 310 also provide barbs 320.

In all the described embodiments, the barbs could be separate elements stitched to the fabric sheet. The advantage of this is that there is no risk of weld fractures.

One practical use of the graft of FIGS. 20a and 20b is as a supra-renal fixation element.

It is envisaged that any of the grafts described herein can be used as an occluder by providing a fabric cover over one of the open ends of the tubular graft. Alternatively, the graft could be used as a platform for the deployment of an artificial valve.

The described embodiments facilitate a significant increase in diameter of the graft over a very short axial length while preserving all the desirable attributed of the graft. An embodiment of a graft with such a dramatic change in diameter is for the endoluminal treatment of an abdominal aortic aneurysm with shape of an "Ali Baba's Basket". In this situation there is essentially no neck to anchor onto between the aneurysm and the renal arteries. The graft can be manufactured and deployed such that it is an optimal fit at the point where the renal arteries branch off and then flares out to match the shape of the top of the aneurysm. This graft would be anchored in position primarily with a supra-renal fixation element.

The stitching used to attach the preform to the graft fabric can be varied in order to optimise mechanical characteristics. Stitches may be triangular or square in order to control the contact area between preform and stitching thread.

The graft may be used in conjunction with a self-sealing element such as an occlusion device. This may be on normal applications of the graft or when used as an occlusion device in conjunction with an occlusion barrier or when used as an artificial vein.

The pattern of preform can be selected in order to create sections along the length of the graft that can vary from being totally flexible to totally supported. In an embodiment used as an occlusion device, two highly supported sections are linked by a highly flexible section which allows the supported sections to deploy perpendicular to the long axis of the vessel irrespective if the tortuosity of the vessel.

The occlusion barrier may be created with a preformed ring of SMA or a circular or spiral pattern that may be embroidered wire or an attached preform in order to improve the seal in a vessel with an irregular cross section.

In all the above-describe embodiments, the fabric seam could be produced by sewing, welding, thermal bonding and by use of adhesives.

What is claimed is:

1. A method for forming a non-expandable reinforced graft including the steps of
   a. providing a sheet of flexible graft material having opposed side edges;
   b. attaching filamentary reinforcement material to the sheet, wherein the filamentary reinforcement material is provided in a pattern including regions:
      (1) extending at least substantially transversely towards a first one of the side edges of the sheet,
      (2) changing direction by approximately 180°, and
      (3) extending at least substantially transversely towards the second one of the side edges of the sheet,
      wherein:
      i. the pattern is repeated to run at least substantially longitudinally with respect to the side edges of the sheet; and
      ii. the filamentary reinforcement material is attached into substantially fixed positions on the sheet, whereby the reinforcement material is not displaceable relative to the sheet;
   c. forming the sheet into an at least substantially tubular shape by bringing together the side edges to form a longitudinal seam.

2. The method of claim 1 wherein the regions in which the filamentary reinforcement material change direction by approximately 180° are U-shaped.

3. The method of claim 1 wherein the reinforcement material is formed from a single wire.

4. The method of claim 1 wherein the sheet of flexible graft material is formed into the tubular shape prior to having the filamentary reinforcement material attached.

5. The method of claim 1 wherein the side edges are brought together in such a manner that the regions in which the filamentary reinforcement material change direction by approximately 180° overlap.

6. The method of claim 5 wherein the overlapping regions in which the filamentary reinforcement material change direction by approximately 180° are sewn to one another.

7. The method of claim 1 wherein the filamentary reinforcement material is attached to the sheet in such a manner that the regions in which the filamentary reinforcement material change direction by approximately 180° overlap.

8. The method of claim 7 wherein the overlapping regions in which the filamentary reinforcement material change direction by approximately 180° are sewn to one another.

9. The method of claim 1 wherein the filamentary reinforcement material is prestressed.

10. A method for forming a non-expandable reinforced graft including the steps of:
    a. providing a sheet of flexible graft material having opposed side edges;
    b. attaching filamentary reinforcement material into substantially fixed positions on the sheet, whereby the reinforcement material is not displaceable relative to the sheet, wherein the filamentary reinforcement material is provided in a pattern including regions:
       (1) extending at least substantially transversely towards a first one of the side edges of the sheet,
       (2) changing direction by approximately 180° to form a bend in the reinforcement material,
       (3) extending at least substantially transversely towards the second one of the side edges of the sheet,
       (4) changing direction by approximately 180° to form another bend,
       wherein the pattern is repeated to run at least substantially longitudinally with respect to the side edges of the sheet; and
    c. forming the sheet into an at least substantially tubular shape by bringing together the side edges to form a longitudinal seam.

11. A method as claimed in claim 10, wherein the sheet is formed into said tubular shape in such a way that bends on either side of the longitudinal seam overlap, oppose, interdigitate or abut.

12. A method as claimed in claim 10, wherein bends at one side of the longitudinal seam are secured to corresponding bends at the other side.

13. The method of claim 10 wherein the filamentary reinforcement material is prestressed.

14. A method for forming a non-expandable reinforced graft including the steps of
    a. providing a sheet of flexible graft material having opposed side edges;
    b. attaching filamentary reinforcement material to the sheet, wherein the filamentary reinforcement material is provided in a pattern including regions:
       (1) extending at least substantially transversely towards a first one of the side edges of the sheet,
       (2) changing direction by approximately 180°, and
       (3) extending at least substantially transversely towards the second one of the side edges of the sheet,
       wherein:
       i. the pattern is repeated to run at least substantially longitudinally with respect to the side edges of the sheet; and
       ii. the regions in which the filamentary reinforcement material change direction by approximately 180° overlap;
    c. forming the sheet into an at least substantially tubular shape by bringing together the side edges to form a longitudinal seam; and
    d. sewing to each other the overlapping regions in which the filamentary reinforcement material change direction by approximately 180°.

15. The method of claim 14 wherein the regions in which the filamentary reinforcement material change direction by approximately 180° are U-shaped.

16. The method of claim 14 wherein the reinforcement material is formed from a single wire.

17. The method of claim 14 wherein the sheet of flexible graft material is formed into the tubular shape prior to having the filamentary reinforcement material attached.

18. The method of claim 14 wherein the filamentary reinforcement material is attached into substantially fixed positions on the sheet, whereby the reinforcement material is not displaceable relative to the sheet.

19. The method of claim 14 wherein the filamentary reinforcement material is prestressed.

20. A method for forming a non-expandable reinforced graft including the steps of:
    a. providing a sheet of flexible graft material having opposed side edges;
    b. attaching filamentary reinforcement material to the sheet, wherein the filamentary reinforcement material is provided in a pattern including regions:
       (1) extending at least substantially transversely towards a first one of the side edges of the sheet,
       (2) changing direction by approximately 180° to form a bend in the reinforcement material, (3) extending at least substantially transversely towards the second one of the side edges of the sheet,
(4) changing direction by approximately 180° to form another bend, wherein the pattern is repeated to run at least substantially longitudinally with respect to the side edges of the sheet; and c. forming the sheet into an at least substantially tubular shape by bringing together the side edges to form a longitudinal seam, wherein bends at one side of the longitudinal seam are secured to corresponding bends at the other side.

21. A method as claimed in claim 20, wherein the sheet is formed into said tubular shape in such a way that bends on either side of the longitudinal seam overlap, oppose, interdigitate or abut.

22. The method of claim 20 wherein the filamentary reinforcement material is attached into substantially fixed positions on the sheet, whereby the reinforcement material is not displaceable relative to the sheet.

23. The method of claim 20 wherein the filamentary reinforcement material is prestressed.

* * * * *